(12) United States Patent
Cassayre et al.

(10) Patent No.: US 7,378,399 B2
(45) Date of Patent: May 27, 2008

(54) AVERMECTINS SUBSTITUTED IN THE 4" AND 4'-POSITIONS HAVING PESTICIDAL PROPERTIES

(75) Inventors: Jerome Cassayre, Basel (CH); Hans Tobler, Basel (CH); Thomas Pitterna, Basel (CH); Peter Maienfisch, Basel (CH); Fiona Murphy Kessabi, Basel (CH); Laura Quaranta, Basel (CH); Ottmar Franz Hueter, Basel (CH)

(73) Assignee: Merial Limited, Duluth, GA (US)

( * ) Notice: Subject to any disclaimer, the term of this patent is extended or adjusted under 35 U.S.C. 154(b) by 471 days.

(21) Appl. No.: 10/544,274

(22) PCT Filed: Feb. 3, 2004

(86) PCT No.: PCT/EP2004/000972

§ 371 (c)(1),
(2), (4) Date: Aug. 3, 2005

(87) PCT Pub. No.: WO2004/069852

PCT Pub. Date: Aug. 19, 2004

(65) Prior Publication Data

US 2006/0154879 A1    Jul. 13, 2006

(30) Foreign Application Priority Data

Feb. 4, 2003    (GB) ................... 0302548.3

(51) Int. Cl.
| | | |
|---|---|---|
| A01N 43/04 | (2006.01) | |
| A01N 43/00 | (2006.01) | |
| A01N 43/40 | (2006.01) | |
| A01N 43/02 | (2006.01) | |
| A01N 43/16 | (2006.01) | |
| A61K 31/40 | (2006.01) | |
| A61K 31/38 | (2006.01) | |
| A61K 31/335 | (2006.01) | |
| A61K 31/35 | (2006.01) | |
| A61K 31/70 | (2006.01) | |
| A61K 31/397 | (2006.01) | |
| A61K 31/445 | (2006.01) | |
| A61K 31/44 | (2006.01) | |
| A01N 43/38 | (2006.01) | |
| A01N 31/40 | (2006.01) | |

(52) U.S. Cl. ............... 514/30; 514/210.01; 514/320; 514/321; 514/337; 514/338; 514/414; 514/430; 514/449; 514/450; 514/459; 504/100

(58) Field of Classification Search ................ 514/280
See application file for complete search history.

(56) References Cited

FOREIGN PATENT DOCUMENTS

WO    WO-02/068442 A    9/2002

OTHER PUBLICATIONS

Jones T K et al: "Synthesis and Biological Activity of 4a,4-Disubstituted Avermectins"; Journal of Agricultural and Food Chem., American Chem. Soc., vol. 42, 1994, p. 1786-1790.

*Primary Examiner*—Johann Richter
*Assistant Examiner*—Courtney A Brown
(74) *Attorney, Agent, or Firm*—Judy Jarecki-Black; Merial Limited; Thomas Kowalski

(57) ABSTRACT

What is described are a compound of the formula (I) Wherein A-B is —CH═CH— or —CH$_2$—CH$_2$—; n is 0 or 1; $R_1$, is $C_1$-$C_{12}$alkyl, $C_3$-$C_8$cycloalkyl or $C_2$-$C_{12}$alkenyl; $R_2$ and $R_3$ for instance are either, (i) independently from each other for instance -Q, —C(═Y)-Q, or —C(═Y)—O-Q; or (ii) together form with the nitrogen atom to which they are bound a three- to seven-membered ring, (iii) together are ═C($R_4$)$R_5$; $R_4$ and $R_5$ are, independently from each other, for instance -Q, —C(═Y)-Q, or —C(═Y)—O-Q; Y is O or S; Q is for instance H or unsubstituted or mono- to penta-substituted $C_1$-$C_{12}$alkyl; or, if appropriate, an E/Z isomer, E/Z isomer mixture and/or tautomer thereof; a process for preparing these compounds, their isomers and tautomers and the use of these compounds, their isomers and tautomers; pesticidal compositions whose active compound is selected from these compounds and their tautomers; intermediates for the preparation of the said compounds of the formula (I), methods for the preparation of the compounds of the formula (I), and a method for controlling pests using these compositions

6 Claims, No Drawings

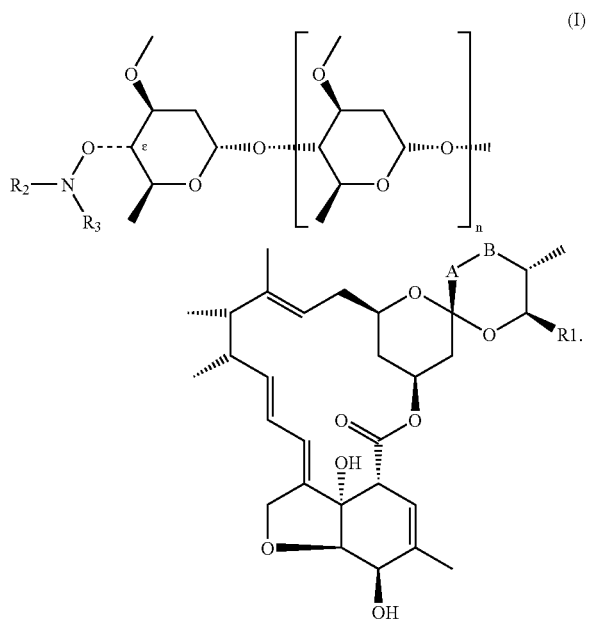

AVERMECTINS SUBSTITUTED IN THE 4" AND 4'-POSITIONS HAVING PESTICIDAL PROPERTIES

This application is a 371 of International Application No. PCT/EP2004/000972 filed Feb. 3, 2004, which claims priority to GB 0302548.3, filed Feb. 4, 2003, the contents of which are incorporated herein by reference.

The invention provides (1) a compound of the formula (I)

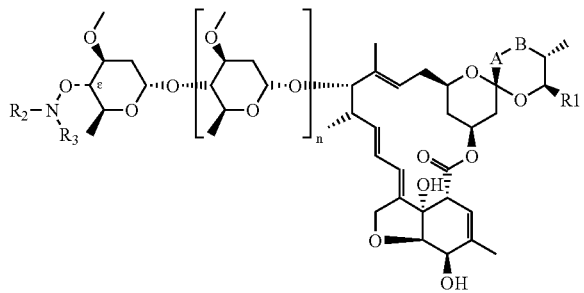

wherein

A-B is —CH=CH— or —CH$_2$—CH$_2$—;

n is 0 or 1;

R$_1$ is C$_1$-C$_{12}$alkyl, C$_3$-C$_8$cycloalkyl or C$_2$-C$_{12}$alkenyl;

R$_2$ and R$_3$ are either, (i) independently from each other, -Q, —C(=Y)-Q, —C(=Y)—O-Q, —C(=Y)—N(R$_6$)-Q, —SO$_2$Q, —SO$_2$N(R$_6$)Q or CN; or (ii) together with the nitrogen atom to which they are bound form a three- to ten-membered ring, which may be monocyclic or bicyclic, which may be saturated or unsaturated, and that may contain, in addition to the aforesaid nitrogen atom, one to two hetero atoms selected from the group consisting of N, O and S, and which is either unsubstituted or independently of one another mono- to pentasubstituted with substituents selected from OH, =O, SH, =S, halogen, CN, SCN, N$_3$, NO$_2$, aryl, C$_1$-C$_{12}$alkyl, C$_3$-C$_8$cycloalkyl, C$_1$-C$_{12}$alkoxy, C$_3$-C$_8$cycloalkoxy, C$_1$-C$_{12}$haloalkoxy, C$_1$-C$_{12}$alkylthio, C$_1$-C$_{12}$cycloalkylthio, C$_1$-C$_{12}$haloalkylthio, C$_1$-C$_6$alkoxy-C$_1$-C$_6$alkyl, C$_2$-C$_8$alkenyl, C$_2$-C$_6$alkenyloxy, C$_2$-C$_6$haloalkenyloxy, C$_2$-C$_8$alkynyl, C$_3$-C$_6$haloalkynyloxy, C$_2$-C$_6$alkenylthio, C$_2$-C$_6$haloalkenylthio, C$_1$-C$_6$alkylsulfinyl, C$_3$-C$_8$cycloalkylsulfinyl, C$_1$-C$_6$haloalkylsulfinyl, C$_3$-C$_8$halocycloalkylsulfinyl, C$_2$-C$_6$alkenylsulfinyl, C$_2$-C$_6$haloalkenylsulfinyl, C$_1$-C$_6$alkylsulfonyl, C$_3$-C$_8$cycloalkylsulfonyl, C$_1$-C$_6$haloalkylsulfonyl, C$_3$-C$_8$halocycloalkylsulfonyl C$_2$-C$_6$alkenylsulfonyl, C$_2$-C$_6$haloalkenylsulfonyl, phenoxy, phenyl-C$_1$-C$_6$alkyl, trialkylsilyl; —C(=O)R$_7$, —O—C(=O)—R$_8$, —NH—C(=O)—R$_8$ and —N(R$_9$)$_2$, wherein the two R$_9$ are independent of each other; or (iii) together are =C(R$_4$)R$_5$;

R$_4$ and R$_5$ are, independently from each other, -Q, —C(=Y)-Q, —C(=Y)—O-Q, —C(=Y)—N(R$_6$)-Q, —SO$_2$Q, —SO$_2$N(R$_6$)Q or CN; or R$_4$ and R$_5$ are together with the carbon atom to which they are bound, a three- to ten-membered alkylene or a four- to seven-membered alkenylene bridge, wherein one CH$_2$ group in the alkylene or alkenylene may have been replaced by O, S or NR$_9$, and which is unsubstituted or mono to trisubstituted;

Y is O or S;

R$_6$ is H, C$_1$-C$_8$alkyl, C$_3$-C$_8$cycloalkyl, C$_2$-C$_8$alkenyl, C$_2$-C$_8$alkynyl, phenyl, benzyl or —C(=O)R$_7$;

Q is H, unsubstituted or mono- to pentasubstituted C$_1$-C$_{12}$alkyl, unsubstituted or mono- to pentasubstituted C$_2$-C$_{12}$alkenyl, unsubstituted or mono- to pentasubstituted C$_2$-C$_{12}$alkynyl, unsubstituted or mono- to pentasubstituted C$_3$-C$_{12}$-cycloalkyl, unsubstituted or mono- to pentasubstituted C$_5$-C$_{12}$-cycloalkenyl, unsubstituted or mono- to pentasubstituted aryl, or unsubstituted or mono- to pentasubstituted heterocyclyl;

and wherein the substituents of the alkyl, alkenyl, alkynyl, alkylene, alkenylene, cycloalkyl, cycloalkenyl, aryl and heterocyclyl radicals mentioned under Q, R$_2$, R$_3$, R$_4$, R$_5$ and R$_6$ are selected from the group consisting of OH, =O, SH, =S, halogen, CN, SCN, SF$_5$, N$_3$, NO$_2$, aryl, C$_3$-C$_8$cycloalkyl, C$_1$-C$_{12}$haloalkyl, C$_3$-C$_8$halocycloalkyl, C$_1$-C$_{12}$alkoxy, C$_3$-C$_8$cycloalkoxy, C$_1$-C$_{12}$haloalkoxy, C$_1$-C$_{12}$alkylthio, C$_1$-C$_{12}$cycloalkylthio, C$_1$-C$_{12}$haloalkylthio, C$_1$-C$_6$alkoxy-C$_1$-C$_6$alkyl, C$_1$-C$_6$alkoxy-C$_1$-C$_6$alkoxy, C$_2$-C$_8$alkenyl, C$_2$-C$_6$alkenyloxy, C$_2$-C$_6$haloalkenyl, C$_2$-C$_6$haloalkenyloxy, C$_2$-C$_8$alkynyl, C$_2$-C$_6$haloalkynyl, C$_3$-C$_6$alkynyloxy, C$_3$-C$_6$haloalkynyloxy, C$_2$-C$_6$alkenylthio, C$_2$-C$_6$haloalkenylthio, C$_1$-C$_6$alkylsulfinyl, C$_3$-C$_8$cycloalkylsulfinyl, C$_1$-C$_6$haloalkylsulfinyl, C$_3$-C$_8$halocycloalkylsulfinyl, C$_2$-C$_6$alkenylsulfinyl, C$_2$-C$_6$haloalkenylsulfinyl, C$_1$-C$_6$alkylsulfonyl, C$_3$-C$_8$cycloalkylsulfonyl, C$_1$-C$_6$haloalkylsulfonyl, C$_3$-C$_8$halocycloalkylsulfonyl C$_2$-C$_6$alkenylsulfonyl, C$_2$-C$_6$haloalkenylsulfonyl, phenoxy, phenyl-C$_1$-C$_6$alkyl, trialkylsilyl; —C(=O)R$_7$, —O—C(=O)—R$_8$, —NH—C(=O)R$_7$, —N(R$_9$)$_2$, wherein the two R$_9$ are independent of each other, aryl, benzyl, heterocyclyl, aryloxy, benzyloxy, heterocyclyloxy, arylthio, benzylthio and heterocyclylthio; wherein the aryl, heterocyclyl, aryloxy, benzyloxy, heterocyclyloxy, arylthio, benzylthio and heterocyclylthio radicals are unsubstituted or, depending on the possibilities of substitution on the ring, are mono- to pentasubstituted by substituents selected from the group consisting of OH, =O, SH, =S, halogen, CN, NO$_2$, C$_1$-C$_{12}$alkyl, C$_1$-C$_{12}$hydroxyalkyl, C$_3$-C$_8$cycloalkyl, C$_1$-C$_{12}$haloalkyl, C$_1$-C$_{12}$alkoxy, C$_1$-C$_{12}$haloalkoxy, C$_1$-C$_{12}$alkylthio, C$_1$-C$_{12}$haloalkylthio, C$_1$-C$_6$alkoxy-C$_1$-C$_6$alkyl, dimethylamino-C$_1$-C$_6$alkoxy, C$_2$-C$_8$alkenyl, C$_2$-C$_8$alkynyl, phenoxy, phenyl-C$_1$-C$_6$alkyl; methylenedioxy, —C(=O)R$_7$, —O—C(=O)—R$_8$, —NH—C(=O)R$_7$, —N(R$_9$)$_2$, wherein the two R$_9$ are independent of each other; C$_1$-C$_6$alkylsulfinyl, C$_3$-C$_8$cycloalkylsulfinyl, C$_1$-C$_6$haloalkylsulfinyl, C$_3$-C$_8$halocycloalkylsulfinyl, C$_1$-C$_6$alkylsulfonyl, C$_3$-C$_8$cycloalkylsulfonyl, C$_1$-C$_6$haloalkylsulfonyl and C$_3$-C$_8$halocycloalkylsulfonyl;

R$_7$ is H, OH, SH, —N(R$_9$)$_2$ wherein the two R$_9$ are independent of each other, C$_1$-C$_{24}$alkyl, C$_2$-C$_{12}$alkenyl, C$_1$-C$_8$hydroxyalkyl, C$_1$-C$_{12}$haloalkyl, C$_1$-C$_{12}$alkoxy, C$_1$-C$_{12}$haloalkoxy, C$_1$-C$_6$alkoxy-C$_1$-C$_6$alkyl, C$_1$-C$_6$alkoxy-C$_1$-C$_6$alkoxy, C$_1$-C$_6$alkoxy-C$_1$-C$_6$alkoxy-C$_1$-C$_6$alkyl, C$_1$-C$_{12}$alkylthio, C$_2$-C$_8$alkenyloxy, C$_3$-C$_8$alkynyloxy; aryl, benzyl, heterocyclyl, aryloxy, benzyloxy, heterocyclyloxy; or aryl, benzyl, heterocyclyl, aryloxy, benzyloxy or heterocyclyloxy, which are mono- to trisubstituted in the ring independently of one another by halogen, nitro, C$_1$-C$_6$alkyl, C$_1$-C$_6$alkoxy, C$_1$-C$_6$haloalkyl or C$_1$-C$_6$haloalkoxy;

R$_8$ is H, C$_1$-C$_6$alkyl that is optionally substituted with one to five substituents selected from the group consisting of halogen, C$_1$-C$_6$alkoxy, hydroxy and cyano, C$_1$-C$_8$-cycloalkyl, aryl, benzyl, heteroaryl; or aryl, benzyl or heteroaryl, which, depending on the possibilities of substitution on the ring, are mono- to trisubstituted by substituents selected from the group consisting of OH, halogen, CN, $NO_2$, $C_1$-$C_{12}$alkyl, $C_1$-$C_{12}$haloalkyl, $C_1$-$C_{12}$alkoxy, $C_1$-$C_{12}$haloalkoxy, $C_1$-$C_{12}$alkylthio and $C_1$-$C_{12}$haloalkylthio; and $R_9$ is H; $C_1$-$C_6$alkyl, which is optionally substituted with one to five substituents selected from the group consisting of halogen, $C_1$-$C_6$alkoxy, hydroxy and cyano; $C_1$-$C_8$-cycloalkyl, aryl, benzyl, heteroaryl; or aryl, benzyl or heteroaryl, which, depending on the possibilities of substitution on the ring, are mono- to trisubstituted by substituents selected from the group consisting of OH, halogen, CN, $NO_2$, $C_1$-$C_{12}$alkyl, $C_1$-$C_{12}$haloalkyl, $C_1$-$C_{12}$alkoxy, $C_1$-$C_{12}$haloalkoxy, $C_1$-$C_{12}$alkylthio and $C_1$-$C_{12}$haloalkylthio;

or, if appropriate, an E/Z isomer, E/Z isomer mixture and/or tautomer thereof, in each case in fro form or in salt form;

a process for preparing these compounds, their isomers and tautomers and the use of these compounds, their isomers and tautomers; pesticides whose active compound is selected from these compounds and their tautomers; and a method for controlling pests using these compositions.

Hereinbefore and hereinafter, the bond at the ε-position marked by the symbol—in formulae (I) to (III) indicates that the (S)— as well as the (R)-isomer is meant.

The literature proposes certain macrolide compounds for controlling pests. However, the biological properties of these known compounds are not entirely satisfactory, and, as a consequence, there is still a need for providing further compounds having pesticidal properties, in particular for the control of insects and representatives of the order Acarina. According to the invention, this object is achieved by providing the present compounds of the formula (I).

The compounds claimed according to the invention are derivatives of Avermectin. Avermectins are known to the person skilled in the art. They are a group of structurally closely related pesticidally active compounds which are obtained by fermenting a strain of the microorganism *Streptomyces avermitilis*. Derivatives of Avermectins can be obtained by conventional chemical syntheses.

The Avermectins which can be obtained from *Streptomyces avermitilis* are referred to as A1a, A1b, A2a, A2b, B1a, B1b, B2a and B2b. The compounds referred to as "A" and "B" have a methoxy radical and an OH group, respectively, in the 5-position. The "a" series and the "b" series are compounds in which the substituent $R_1$ (in position 25) is a sec-butyl radical and an isopropyl radical, respectively. The number 1 in the name of the compounds means that carbon atoms 22 and 23 are linked by double bonds; the number 2 means that they are linked by a single bond and that the C atom 23 carries an OH group. The above nomenclature is adhered to in the description of the present invention to denote the specific structure type in the not naturally occurring Avermectin derivatives according to the invention which corresponds to the naturally occurring Avermectin. What is for instance claimed according to the invention are derivatives of compounds of the B1 series, in particular mixtures of derivatives of Avermectin B1, especially B1a and B1b, along with derivatives having a single bond between carbon atoms 22 and 23, and derivatives having other substituents in the 25-position, as well as the corresponding monosaccharides.

Some of the compounds of the formula (I) can be present as tautomers. Accordingly, hereinabove and hereinbelow, the compounds of the formula (I) are, if appropriate, also to be understood as including the corresponding tautomers, even if the latter are not specifically mentioned in each case.

The compounds of formula (I) and, where applicable, their tautomers can form salts, for example acid addition salts. These acid addition salts are formed, for example, with strong inorganic acids, such as mineral acids, for example sulfuric acid, a phosphoric acid or a hydrohalic acid, with strong organic carboxylic acids, such as unsubstituted or substituted, for example halo-substituted, $C_1$-$C_4$alkanecarboxylic acids, for example acetic acid, unsaturated or saturated dicarboxylic acids, for example oxalic acid, malonic acid, maleic acid, fumaric acid or phthalic acid, hydroxycarboxylic acids, for example ascorbic acid, lactic acid, malic acid, tartaric acid or citric acid, or benzoic acid, or with organic sulfonic acids, such as unsubstituted or substituted, for example halo-substituted, $C_1$-$C_4$alkane- or aryl-sulfonic acids, for example methane- or p-toluene-sulfonic acid. Compounds of formula (I) that have at least one acidic group can furthermore form salts with bases. Suitable salts with bases are, for example, metal salts, such as alkali metal salts or alkaline earth metal salts, for example sodium, potassium or magnesium salts, or salts with ammonia or with an organic amine, such as morpholine, piperidine, pyrrolidine, a mono-, di- or tri-lower alkylamine, for example ethylamine, diethylamine, triethylamine or dimethylpropylamine, or a mono-, di- or trihydroxy-lower alkylamine, for example mono-, di- or tri-ethanolamine. Corresponding internal salts may also be formed where appropriate. The free form is preferred. Among the salts of the compounds of formula (I), the agrochemically advantageous salts are preferred. Hereinbefore and hereinafter, any reference to the free compounds of formula (I) or their salts is to be understood as including, where appropriate, also the corresponding salts or the free compounds of formula (I), respectively. The same applies to tautomers of compounds of formula (I) and salts thereof.

Unless defined otherwise, the general terms used hereinabove and hereinbelow have the meanings given below.

Unless defined otherwise, carbon-containing groups and compounds each contain from 1 up to and including 6, preferably from 1 up to and including 4, especially 1 or 2, carbon atoms.

Halogen—as a group per se and also as a structural element of other groups and compounds, such as haloalkyl, haloalkoxy and haloalkylthio—is fluorine, chlorine, bromine or iodine, in particular fluorine, chlorine or bromine, especially fluorine or chlorine.

Alkyl—as a group per se and also as a structural element of other groups and compounds, such as haloalkyl, alkoxy and alkylthio—is, in each case taking into account the number of carbon atoms contained in each case in the group or compound in question, either straight-chain, i.e. methyl, ethyl, propyl, butyl, pentyl, hexyl, heptyl or octyl, or branched, for example isopropyl, isobutyl, sec-butyl, tert-butyl, isopentyl, neopentyl or isohexyl.

Cycloalkyl—as a group per se and also as a structural element of other groups and compounds, such as, for example, of halocycloalkyl, cycloalkoxy and cycloalkylthio—is, in each case taking into account the number of carbon atoms contained in each case in the group or compound in question, cyclopropyl, cyclobutyl, cyclopentyl, cyclohexyl, cycloheptyl or cyclooctyl.

Alkenyl—as a group per se and also as a structural element of other groups and compounds—is, taking into account the number of carbon atoms and conjugated or isolated double bonds contained in the group, either straight-chain, for example vinyl, allyl, 2-butenyl, 3-pentenyl, 1-hexenyl, 1-heptenyl, 1,3-hexadienyl or 1,3-octadienyl, or branched, for example isopropenyl, isobutenyl, isoprenyl, tert-pentenyl, isohexenyl, isoheptenyl or isooctenyl. Preference is given to alkenyl groups having 3 to 12, in particular 3 to 6, especially 3 or 4, carbon atoms.

Alkynyl—as a group per se and also as a structural element of other groups and compounds—is, in each case taking into account the number of carbon atoms and conjugated or isolated double bonds contained in the group or compound in question, either straight-chain, for example ethynyl, propargyl, 2-butynyl, 3-pentynyl, 1-hexynyl, 1-heptynyl, 3-hexen-1-ynyl or 1,5-heptadien-3-ynyl, or branched, for example 3-methylbut-1-ynyl, 4-ethylpent-1-ynyl, 4-methylhex-2-ynyl or 2-methylhept-3-ynyl. Preference is given to groups —$CH_2$—$C_2$-$C_{11}$alkynyl, in particular —$CH_2$— $C_2$-$C_5$alkynyl, especially —$CH_2$—$C_2$-$C_3$alkynyl.

Alkylene and alkenylene are straight-chain or branched bridge members; they are in particular —$CH_2$—$CH_2$—$CH_2$—, —$CH_2$—$CH_2$—$CH_2$—$CH_2$—, —$CH_2$—$CH_2$—$CH_2$—$CH_2$—$CH_2$—, —$CH_2(CH_3)CH_2$—$CH_2$—, —$CH_2C(CH_3)_2$—$CH_2$—, —$CH_2$—CH=CH—, —$CH_2$—CH=CH—$CH_2$— or —$CH_2$—CH=CH—$CH_2$—$CH_2$—.

Halogen-substituted carbon-containing groups and compounds, such as, for example, halogen-substituted alkyl, alkenyl, alkynyl, cycloalkyl, alkoxy or alkylthio, can be partially halogenated or perhalogenated, where in the case of polyhalogenation the halogen substituents can be identical or different. Examples of haloalkyl—as a group per se and also as a structural element of other groups and compounds, such as haloalkoxy or haloalkylthio—are methyl which is mono- to trisubstituted by fluorine, chlorine and/or bromine, such as $CHF_2$ or $CF_3$; ethyl which is mono- to pentasubstituted by fluorine, chlorine and/or bromine, such as $CH_2CF_3$, $CF_2CF_3$, $CF_2CCl_3$, $CF_2CHCl_2$, $CF_2CHF_2$, $CF_2CFCl_2$, $CF_2CHBr_2$, $CF_2CHClF$, $CF_2CHBrF$ or $CClFCHClF$; propyl or isopropyl which is mono- to heptasubstituted by fluorine, chlorine and/or bromine, such as $CH_2CHBrCH_2Br$, $CF_2CHFCF_3$, $CH_2CF_2CF_3$, $CF(CF_3)_2$ or $CH(CF_3)_2$; butyl or one of its isomers, mono- to nonasubstituted by fluorine, chlorine and/or bromine, such as $CF(CF_3)CHFCF_3$ or $CH_2(CF_2)_2CF_3$; pentyl or one of its isomers, mono- to undecasubstituted by fluorine, chlorine and/or bromine, such as $CF(CF_3)(CHF_2)CF_3$ or $CH_2(CF_2)_3CF_3$; and hexyl or one of its isomers, mono- to tridecasubstituted by fluorine, chlorine and/or bromine, such as $(CH_2)_4CHBrCH_2Br$, $CF_2(CHF)_4CF_3$, $CH_2(CF_2)_4CF_3$ or $C(CF_3)_2(CHF)_2CF_3$.

Aryl is in particular phenyl, naphthyl, anthracenyl, phenanthrenyl, perylenyl or fluorenyl, preferably phenyl.

Heterocyclyl is understood as being a three- to seven-membered monocyclic ring, which may be saturated or unsaturated, and that contains from one to three hetero atoms selected from the group consisting of N, O and S, especially N and S; or a bicyclic ring-system having from 8 to 14 ring atoms, which may be saturated or unsaturated, and that may contain either in only one ring or in both rings independently of one another, one or two hetero atoms selected from N, O and S.

Heterocyclyl is in particular piperidinyl, piperazinyl, oxiranyl, morpholinyl, thiomorpholinyl, pyridyl, N-oxidopyridinio, pyrimidyl, pyrazinyl, s-triazinyl, 1,2,4-triazinyl, thienyl, furanyl, dihydrofuranyl, tetrahydrofuranyl, pyranyl, tetrahydropyranyl, pyrrolyl, pyrrolinyl, pyrrolidinyl, pyrazolyl, imidazolyl, imidazolinyl, thiazolyl, isothiazolyl, triazolyl, oxazolyl, thiadiazolyl, thiazolinyl, thiazolidinyl, oxadiazolyl, maleimidoyl, succinimidoyl, phthalimidoyl, benzothienyl, quinolinyl, quinoxalinyl, benzofuranyl, benzimidazolyl, benzpyrrolyl, benzthiazolyl, indolinyl, isoindolinyl, cumarinyl, indazolyl, benzothiophenyl, benzofuranyl, pteridinyl or purinyl, which are preferably attached via a C atom; thienyl, benzofuranyl, benzothiazolyl, tetrahydropyranyl or indolyl is preferred; in particular pyridyl or thiazolyl. The said heterocyclyl radicals may preferably be unsubstituted or—depending on the substitution possibilities on the ring system—substituted by 1 to 4 substituents selected from the group consisting of halogen, =O, —OH, =S, SH, nitro, $C_1$-$C_6$alkyl, $C_1$-$C_6$hydroxyalkyl, $C_1$-$C_6$alkoxy, $C_1$-$C_6$haloalkyl, $C_1$-$C_6$haloalkoxy, phenyl, benzyl, —C(=O)—$R_8$ and —$CH_2$—C(=O)—$R_8$.

In the context of the present invention, preference is given to (2) compounds according to group (1) of the formula (I) in which $R_1$ is isopropyl or sec-butyl, preferably to those in which a mixture of the isopropyl and the sec-butyl derivative is present;

(3) compounds according to group (1) of the formula (I) in which $R_1$ is cyclohexyl;

(4) compounds according to group (1) of the formula (I) in which $R_1$ is 1-methyl-butyl;

(5) compounds according to one of groups (1) to (4) of the formula (I) in which the configuration at the ∈-position is (S);

(6) compounds according to one of groups (1) to (4) of the formula (I) in which the configuration at the ∈-position is (R);

(7) compounds according to one of groups (1) to (6) of the formula (I) in which n is 1;

(8) compounds according to one of groups (1) to (6) of the formula (I) in which n is 0;

(9) compounds according to one of groups (1) to (8) of the formula (I) in which A-B is —CH=CH—;

(10) compounds according to one of groups (1) to (8) of the formula (I) in which A-B is —$CH_2$—$CH_2$—;

(11) compounds according to one of groups (1) to (10) of the formula (I) in which $R_2$ is -Q;

(12) compounds according to one of groups (1) to (10) of the formula (I) in which $R_2$ is —C(=O)-Q, —C(=O)—O-Q, —C(=O)—N($R_6$)-Q, —$SO_2$Q or —$SO_2$N($R_6$)Q;

(13) compounds according to one of groups (1) to (12) of the formula (I) in which $R_3$H, unsubstituted or mono- to pentasubstituted $C_1$-$C_{12}$alkyl, unsubstituted or mono- to pentasubstituted $C_2$-$C_{12}$alkenyl;

(14) compounds according to one of groups (1) to (10) of the formula (I) in which $R_2$ and $R_3$ together form with the nitrogen atom to which they are bound a five- to seven-membered ring, which may be monocyclic or bicyclic, which may be saturated or unsaturated, and that may contain, in addition to the aforesaid nitrogen atom, one or two hetero atoms selected from the group consisting of N, O and S, and which is either unsubstituted or independently of one another mono-trisubstituted with substituents selected from OH, =O, SH, =S, halogen, CN, $NO_2$, aryl, $C_1$-$C_{12}$alkyl, $C_3$-$C_8$cycloalkyl, $C_1$-$C_{12}$haloalkyl, $C_1$-$C_{12}$alkoxy, $C_1$-$C_{12}$haloalkoxy, $C_1$-$C_{12}$alkylthio, $C_1$-$C_{12}$haloalkylthio;

(15) compounds according to one of groups (1) to (10) or (14) of the formula (I) in which $R_2$ and $R_3$ together are a four- to six membered alkylene bridge, which is unsubstituted or mono to tri-substituted; especially unsubstituted;

(16) compounds according to one of groups (1) to (10), (14) or (15) of the formula (I) in which and $NR_2R_3$ is phtalimidoyl, maleimidoyl, succinimidoyl, which are unsubstituted or mono- to tetrasubstituted in the ring independently of one another by OH, halogen, CN, $NO_2$, aryl, $C_1$-$C_{12}$alkyl, $C_3$-$C_8$cycloalkyl, $C_1$-$C_{12}$haloalkyl, $C_1$-$C_{12}$alkoxy, $C_1$-$C_{12}$haloalkoxy, $C_1$-$C_{12}$alkylthio, $C_1$-$C_{12}$haloalkylthio, $C_1$-$C_6$alkoxy-$C_1$-$C_6$alkyl, $C_2$-$C_8$alkenyl, $C_2$-$C_8$alkynyl, phenoxy, phenyl-$C_1$-$C_6$alkyl; —C(=O)$R_7$, —O—C(=O)—$R_8$, —NH—C(=O)$R_8$, —N($R_9$)$_2$, wherein the two $R_9$ are independent of each other; $C_1$-$C_6$alkylsulfinyl, $C_3$-$C_8$cycloalkylsulfinyl, $C_1$-$C_6$haloalkylsulfinyl, $C_3$-$C_8$halocycloalkylsulfinyl, $C_1$-$C_6$alkylsulfonyl, $C_3$-$C_8$cycloalkylsulfonyl, $C_1$-$C_6$haloalkylsulfonyl and $C_3$-$C_8$halocycloalkylsulfonyl;

(17) compounds according to one of groups (1) to (13) of the formula (I) in which Q is unsubstituted or mono-substituted aryl or unsubstituted or mono-substituted heterocyclyl;

(18) compounds according to one of groups (1) to (13) of the formula (I) in which Q is H, $C_1$-$C_{12}$alkyl, $C_2$-$C_{12}$alkenyl, $C_3$-$C_{12}$alkynyl or $C_3$-$C_{12}$-cycloalkyl, which are all unsubstituted; preferably H or $C_1$-$C_{12}$alkyl;

(19) compounds according to one of groups (1) to (13) of the formula (I) in which Q is $C_3$-$C_{12}$-cycloalkyl, $C_5$-$C_{12}$-cycloalkenyl, aryl or heterocyclyl, which are all unsubstituted.

Special preference is given within the scope of the invention to the compounds of formula (I) listed in the Tables and, where applicable, their tautomers, their mixtures of tautomers, their E/Z isomers, mixtures of E/Z isomers and diastereomers.

The invention also provides a process for preparing the compounds of the formula (I) and, if appropriate, tautomers thereof, wherein $R_2$ and $R_3$ are defined as under (1) which comprises (A) reacting a compound of formula (II)

wherein n and A-B are as defined in formula (I), G is a protecting group and Z is a leaving group such as chloride, bromide, iodide, alkylsulfonate, haloalkylsulfonate or arylsulfonate, and which is known or can be prepared by methods known per se, with a compound of formula $R_2R_3$NOH in which $R_2$ and $R_3$ have the meanings as given above for formula (I) under (1), to form a compound of the formula (III)

wherein $R_2$, $R_3$, n, A-B are as defined for formula (I) and G is a protecting group; and (B) removing the protecting group G of the compound of formula (III) so obtained, or (C) for preparing a compound of the formula (I) wherein $R_1$, n and A-B are as defined for formula (I) and $R_2$ and $R_3$ are H, reacting a compound of formula (I), wherein $R_1$, n and A-B are as defined for formula (I) under (1), and $R_2$ and $R_3$ are as defined for formula (I) under (ii), with a compound of formula (Q)$_2$N—NH$_2$, or with a compound of formula Q-NH$_2$, in which the substituents Q independently of each other have the same meaning as given above under (1) for formula (I), or with a reducing agent; or (D) for forming a compound of the formula (I), wherein $R_1$, n and A-B are as defined for formula (I) and $R_2$ and $R_3$ have the meaning as defined under (iii) for formula (I), reacting a compound of formula (I), in which n, A-B and $R_1$ have the same meanings as given above under (1) for formula (I) and $R_2$ and $R_3$ are H, with a compound $R_4$—CO—$R_5$, in which $R_4$ and $R_5$ have the same meanings as given above under (iii) for formula (I);

(E) for forming a compound of the formula (I), wherein $R_1$, n and A-B are as defined for formula (I) and $R_2$ and $R_3$ have the meanings as defined under (i) for formula (I), reacting a compound of formula (I), in which n, A-B, and $R_1$ have the same meanings as given above under (1) for formula (I), and $R_2$ and $R_3$ are H, with a compound Q-$X_2$, with a compound Q-C(=O)—Cl, Q-O—C(=O)—Cl, Q-C(=S)—Cl, Q-O—C(=S)—Cl, Q-SO$_2$—Cl, Q-N($R_6$)—SO$_2$—Cl, Q-N($R_6$)—C(=O)—Cl, Q-N($R_6$)—C(=S)—Cl, Q-N=C=O or with a compound Q-N=C=S, in which Q and $R_6$ have the same meaning as given above under (1) for formula (I) and $X_2$ is chloride, bromide, iodide, alkylsulfonate, haloalkylsulfonate or arylsulfonate, or (F) reacting a compound of formula (III), in which n, A-B, $R_1$ and G have the same meanings as given above under (A) for formula (III) and in which $R_2$ and $R_3$ are H with a compound of the formula Q-$X_2$, Q-C(=O)—Cl, Q-O—C(=O)—Cl, Q-C(=S)—Cl, Q-O—C(=S)—Cl, Q-SO$_2$—Cl, Q-N($R_6$)—SO$_2$—Cl, Q-N($R_6$)—C(=O)—Cl, Q-N($R_6$)—C(=S)—Cl, Q-N=C=O or Q-N=C=S, in which Q and $R_6$ have—with the exception of H—the same meaning as given above under (1) for formula (I) and $X_2$ is chloride, bromide, iodide, alkylsulfonate, haloalkylsulfonate or arylsulfonate, to form a compound of formula (III), in which n, A-B, $R_1$ and G have the same meanings as given above for formula (III), and in which $R_2$ and $R_3$ have the same meanings as given above under (i) for formula (I), provided that at least one of the substituents is not H; and (G) removing the protecting group G of the compound of formula (III) so obtained, as described under (B), to form a compound of formula (I).

The reactions described hereinabove and hereinbelow are carried out in a manner known per se, for example in the absence or, customarily, in the presence of a suitable solvent or diluent or of a mixture thereof, the reactions being carried out, as required, with cooling, at room temperature or with heating, for example in a temperature range of approximately from −80° C. to the boiling temperature of the reaction medium, preferably from approximately 0° C. to approximately +150° C., and, if necessary, in a closed vessel, under pressure, under an inert gas atmosphere and/or under anhydrous conditions. Especially advantageous reaction conditions can be found in the Examples.

The reaction time is not critical; a reaction time of from about 0.1 to about 24 hours, especially from about 0.5 to about 10 hours, is preferred.

The product is isolated by customary methods, for example by means of filtration, crystallisation, distillation or chromatography, or any suitable combination of such methods.

The starting materials mentioned hereinabove and hereinbelow that are used for the preparation of the compounds of formula (I) and, where applicable, their tautomers are known or can be prepared by methods known per se, e.g. as indicated below.

Process Variant (A):

Examples of solvents and diluents include: aromatic, aliphatic and alicyclic hydrocarbons and halogenated hydrocarbons, such as benzene, toluene, xylene, mesitylene, tetraline, chlorobenzene, dichlorobenzene, bromobenzene, petroleum ether, hexane, cyclohexane, dichloromethane, trichloromethane, tetrachloromethane, dichloroethane, trichloroethene or tetrachloroethene; ethers, such as diethyl ether, dipropyl ether, diisopropyl ether, dibutyl ether, tert-butyl methyl ether, ethylene glycol monomethyl ether, ethylene glycol monoethyl ether, ethylene glycol dimethyl ether, dimethoxydiethyl ether, tetrahydrofuran or dioxane; alcohols, such as methanol, ethanol, propanol, isopropanol, butanol, ethylene glycol or glycerol; carboxylic acids, such as acetic acid, pivalic acid or formic acid; ketones, such as acetone, methyl ethyl ketone or methyl isobutyl ketone; carboxylic acid esters, such as methyl acetate, ethyl acetate, or esters of benzoic acid; amides, such as N,N-dimethylformamide, N,N-diethylformamide, N,N-dimethylacetamide, N-methylpyrrolidone or hexamethylphosphoric acid triamide; nitriles, such as acetonitrile or propionitrile; and sulfoxides, such as dimethyl sulfoxide; and also water; or mixtures of the mentioned solvents; Preference is given to ethers, nitriles and amides, or mixtures thereof; acetonitrile is especially preferred.

Protecting groups G in the compounds of formulae (II) and (III) include: alkyl ether radicals, such as methoxymethyl, methylthiomethyl, tert-butylthiomethyl, benzyloxymethyl, p-methoxybenzyl, 2-methoxyethoxymethyl, 2,2,2-trichloroethoxymethyl, 2-(trimethylsilyl)ethoxymethyl, tetrahydropyranyl, tetrahydrofuranyl, 1-ethoxyethyl, 1-(2-chloroethoxy)ethyl, 1-methyl-1-methoxyethyl, 1-methyl-1-benzyloxyethyl, trichloroethyl, 2-trimethylsilylethyl, tert-butyl, allyl, p-methoxyphenyl, 2,4-dinitrophenyl, benzyl, p-methoxybenzyl, o-nitrobenzyl, p-nitrobenzyl, triphenylmethyl; trialkylsilyl radicals, such as trimethylsilyl, triethylsilyl, dimethyl-tert-butylsilyl, dimethyl-isopropylsilyl, dimethyl-1,1,2-trimethylpropylsilyl, diethyl-isopropylsilyl, dimethyl-tert-hexylsilyl, but also phenyl-tert-alkylsilyl groups, such as diphenyl-tert-butylsilyl; esters, such as formates, acetates, chloroacetates, dichloroacetates, trichloroacetates, trifluoroacetates, methoxyacetates, phenoxyacetates, pivaloates, benzoates; alkyl carbonates, such as methyl-, 9-fluorenylmethyl-, ethyl-, 2,2,2-trichloroethyl-, 2-(trimethylsilyl)ethyl-, vinyl-, allyl-, benzyl-, p-methoxybenzyl-, o-nitrobenzyl-, p-nitrobenzyl-, but also p-nitrophenyl-carbonate.

Preference is given to trialkylsilyl radicals, such as trimethylsilyl, triethylsilyl, dimethyl-tert-butylsilyl, diphenyl-tert-butylsilyl, esters, such as methoxyacetates and phenoxyacetates, and carbonates, such as 9-fluorenylmethylcarbonates and allylcarbonates. Dimethyl-tert-butylsilyl ether is especially preferred.

The reactions are advantageously carried out in a temperature range of from about −70° C. to the boiling point of the solvent used; preference being given to reaction at −10° C. to 25° C.; in the presence of a base, for example an inorganic base, such as sodium hydroxide, potassium hydroxide, sodium carbonate or sodium bicarbonate, or an organic base, such as pyridine, triethylamine, N-ethyl-N,N-diisopropylamine, 1,8-diazabicyclo[5.4.0]undec-7-ene, or 1,5-diazabicyclo[4.3.0]non-5-ene; or without the presence of a base; preference being given to 1,8-diazabicyclo[5.4.0]undec-7-ene.

Examples of a compound $R_2R_3N$—OH include substituted or unsubstituted N-hydroxymaleimides and N-hydroxyphtalimides, for example N-hydroxyphtalimide.

In a preferred embodiment of Variant (A) the reaction is carried out with N-hydroxyphtalimide at 0° C., in acetonitrile in the presence of 1,8-diazabicyclo[5.4.0]undec-7-ene.

Especially preferred conditions for this process variant are described in Examples A2.1 and A4.1.

Process Variant (B):

Examples of solvents and diluents are the same as those mentioned under Process variant A. Preference is given to ethers; tetrahydrofuran is especially preferred.

The reactions are advantageously carried out in a temperature range of approximately from −70° C. to 100° C., preferably at from −10° C. to 25° C.

There are suitable for the removal of the protecting group Lewis acids, such as hydrochloric acid, methanesulfonic acid, $BF_3*OEt_2$, HF in pyridine, $Zn(BF_4)_2*H_2O$, p-toluenesulfonic acid, $AlCl_3$, $HgCl_2$; ammonium fluoride, such as tetrabutylammonium fluoride; bases, such as ammonia, trialkylamine or heterocyclic bases; hydrogenolysis with a catalyst, such as palladium-on-carbon; reducing agents, such as sodium borohydride or tributyltin hydride with a catalyst, such as $Pd(PPh_3)_4$, or also zinc with acetic acid.

Preference is given to acids, such as methanesulfonic acid or HF in pyridine; sodium borohydride with Pd(0); bases, such as ammonia, triethylamine or pyridine; especially acids, such as HF in pyridine or methanesulfonic acid.

In a preferred embodiment of variant (B) the reaction is carried out with HF in pyridine at room temperature, in tetrahydrofuran.

Especially preferred conditions for the reaction are described in Example A2.1 and A4.1.

Process Variant (C):

Examples of solvents and diluents are the same as those mentioned under Process variant A. Preference is given to alcohols; ethanol is especially preferred.

The reactions are advantageously carried out in a temperature range of from about −70° C. to the boiling point of the solvent used; preference being given to reaction at 0° C. to 30° C.;

Examples of compounds of the formula $(Q)_2N-NH_2$ include hydrazines, for example hydrazine or methylhydrazine.

Examples of reducing agents are known to a person skilled in the art, they include hydrides; especially suitable are borohydrides, for example sodium borohydride or sodium cyanoborohydride.

In a preferred embodiment of variant (C) the reaction is carried out with hydrazine monohydrate at room temperature, in ethanol.

Especially preferred conditions for the reaction are described in Example A2.2 and A4.2.

Process Variant (D):

Examples of solvents and diluents are the same as those mentioned under Process variant A. Preference is given to aromatic hydrocarbons, or mixtures thereof; toluene, dioxan and water are especially preferred.

The reactions are advantageously carried out in a temperature range of from about −70° C. to the boiling point of the solvent used; preference being given to reaction at 25° C. to 80° C.; in the presence of a catalyst such as pyridinium p-toluenesulfonate; or without a catalyst.

Examples of compound $R_4-CO-R_5$ include ketones and aldehydes, for example acetaldehyde, glycolaldehyde, glyoxylic acid, benzaldehyde, acetone or cyclopentanone.

In a preferred embodiment of variant (D) the reaction is carried out in toluene at room temperature in the presence of pyridinium p-toluene sulfonate.

In another preferred embodiment of variant (D) the reaction is carried out in dioxan and water at room temperature in the presence of pyridinium p-toluene sulfonate.

In another preferred embodiment of variant (D) the reaction is carried out in toluene at room temperature.

Especially preferred conditions for the reaction are described in Example A1.1, A1.2, A1.13 and A1.16.

Process Variant (E):

Examples of solvents and diluents are the same as those mentioned under Process variant A. Preference is given to esters and water, or mixtures thereof; ethyl acetate and water are especially preferred.

The reactions are advantageously carried out in a temperature range of from about −70° C. to the boiling point of the solvent used; preference being given to reaction at 25° C. to 80° C.; in the presence of a base, for example an inorganic base, such as sodium hydroxide, potassium hydroxide, sodium carbonate or sodium bicarbonate, or an organic base, such as pyridine, triethylamine, N-ethyl-N,N-diisopropylamine, 1,8-diazabicyclo[5.4.0]undec-7-ene, or 1,5-diazabicyclo[4.3.0]non-5-ene; or without the presence of a base; preference being given to sodium bicarbonate.

In a preferred embodiment of Variant (E) the reaction is carried out in the presence of bicarbonate at room temperature, in a mixture of ethyl acetate and water as the solvent.

Especially preferred conditions for the reaction are described in Example A2.11.

Process Variant (F):

Examples of solvents and diluents are the same as those mentioned under Process variant A. Preference is given to halogenated hydrocarbons, or mixtures thereof; dichloromethane is especially preferred.

The reactions are advantageously carried out in a temperature range of from about −70° C. to the boiling point of the solvent used; preference being given to reaction at 25° C. to 80° C.; in the presence of a base, for example an inorganic base, such as sodium hydroxide, potassium hydroxide, sodium carbonate or sodium bicarbonate, or an organic base, such as pyridine, triethylamine, N-ethyl-N,N-diisopropylamine, 1,8-diazabicyclo[5.4.0]undec-7-ene, or 1,5-diazabicyclo[4.3.0]non-5-ene; or without the presence of a base; preference being given to pyridine.

In a preferred embodiment of Variant (E) the reaction is carried out in the presence of bicarbonate at room temperature, in a mixture of ethyl acetate and water as the solvent.

Especially preferred conditions for the reaction are described in Example A2.11.

Process Variant (G) is Carried Out by Analogy to Process Variant (B).

The comments made above in connection with tautomers of compounds of the formula (I) apply analogously to the staring materials and intermediates mentioned hereinbefore and hereinbelow with respect to their tautomers.

The compounds of formula (I) may be in the form of one of the possible isomers or in the form of a mixture thereof, in the form of pure isomers or in the form of an isomeric mixture, i.e. in the form of a diastereomeric mixture; the invention relates both to the pure isomers and to the diastereomeric mixtures and is to be interpreted accordingly hereinabove and hereinbelow, even if stereochemical details are not mentioned specifically in every case.

The diastereomeric mixtures can be resolved into the pure isomers by known methods, for example by recrystallisation from a solvent, by chromatography, for example high pressure liquid chromatography (HPLC) on acetylcellulose, with the aid of suitable microorganisms, by cleavage with specific, immobilised enzymes, or via the formation of inclusion compounds, for example using crown ethers, only one isomer being complexed.

Apart from the separation of corresponding mixtures of isomers, pure diasteroisomers can be obtained according to the invention also by generally known methods of stereoselective synthesis, for example by carrying out the process according to the invention using starting materials having correspondingly suitable stereochemistry.

In each case it is advantageous to isolate or synthesize the biologically more active isomer, where the individual components have different biological activity.

The compounds of formula (I) may also be obtained in the form of their hydrates and/or may include other solvents, for example solvents which may have been used for the crystallisation of compounds in solid form.

The invention relates to all those embodiments of the process according to which a compound obtainable as starting material or intermediate at any stage of the process is used as starting material and all or some of the remaining steps are carried out, or in which a starting material is used in the form of a derivative and/or a salt and/or its diastereomers, or, especially, is formed under the reaction conditions. For instance compounds of formula (I) bearing a functional group in its free or protected form can be used as starting materials for the preparation of further compounds of formula (I). For such manipulations methods known to the person skilled in the art can be applied.

In the processes of the present invention it is preferable to use those starting materials and intermediates which result in the compounds of formula (I) that are especially preferred.

The invention relates especially to the preparation processes described in the Examples.

In the area of pest control, the compounds of formula (I) according to the invention are active ingredients exhibiting valuable preventive and/or curative activity with a very advantageous biocidal spectrum and a very broad spectrum, even at low rates of concentration, while being well tolerated by warm-blooded animals, fish and plants. They are, surprisingly, equally suitable for controlling both plant pests and ecto- and endo-parasites in humans and more especially in productive livestock, domestic animals and pets. They are effective against all or individual development stages of normally sensitive animal pests, but also of resistant animal pests, such as insects and representatives of the order Acarina, nematodes, cestodes and trematodes, while at the same time protecting useful organisms. The insecticidal or acaricidal activity of the active ingredients according to the invention may manifest itself directly, i.e. in the mortality of the pests, which occurs immediately or only after some time, for example during moulting, or indirectly, for example in reduced oviposition and/or hatching rate. Good activity corresponds to a mortality of at least 50 to 60%.

Successful control within the scope of the subject of the invention is possible, in particular, of pests from the orders Lepidoptera, Coleoptera, Orthoptera, Isoptera, Psocoptera, Anoplura, Mallophaga, Thysanoptera, Heteroptera, Homoptera, Hymenoptera, Diptera, Siphonaptera, Thysanura and Acarina, mainly Acarina, Diptera, Thysanoptera, Lepidoptera and Coleoptera. Very especially good control is possible of the following pests:

*Abagrotisi* spp., *Abraxas* spp., *Acantholeucania* spp., *Acanthoplusia* spp., *Acarus* spp., *Acarus siro*, *Aceria* spp., *Aceria sheldoni*, *Acleris* spp., *Acoloithus* spp., *Acompsia* spp., *Acossus* spp., *Acria* spp., *Acrobasis* spp., *Acrocercops* spp., *Acrolepia* spp., *Acrolepiopsis* spp., *Acronicta* spp., *Acropolitis* spp., *Actebia* spp., *Aculus* spp., *Aculus schlechtendali*, *Adoxophyes* spp., *Adoxophyes reticulana*, *Aedes* spp., *Aegeria* spp., *Aethes* spp., *Agapeta* spp., *Agonopterix* spp., *Agriopis* spp., *Agriotes* spp., *Agriphila* spp., *Agrochola* spp., *Agroperina* spp., *Alabama* spp., *Alabama argillaceae*, *Agrotis* spp., *Albuna* spp., *Alcathoe* spp., *Alcis* spp., *Aleimma* spp., *Aletia* spp., *Aleurothrixus* spp., *Aleurothrixus floccosus*, *Aleyrodes* spp., *Aleyrodes brassicae*, *Allophyes* spp., *Alsophila* spp., *Amata* spp., *Amathes* spp., *Amblyomma* spp., *Amblyptilia* spp., *Ammoconia* spp., *Amorbia* spp., *Amphion* spp., *Amphipoea* spp., *Amphipyra* spp., *Amyelois* spp., *Anacamptodes* spp., *Anagrapha* spp., *Anarsia* spp., *Anatrychyntis* spp., *Anavitrinella* spp., *Ancylis* spp., *Andropolia* spp., *Anhimella* spp., *Antheraea* spp., *Antherigona* spp., *Antherigona soccata*, *Anthonomus* spp., *Anthonomus grandis*, *Anticarsia* spp., *Anticarsia gemmatalis*, *Aonidiella* spp., *Apamea* spp., *Aphania* spp., *Aphelia* spp., *Aphididae*, *Aphis*spp., *Apotomis* spp., *Aproaerema* spp., *Archippus* spp., *Archips* spp., *Acromyrmex*, *Arctia* spp., *Argas* spp., *Argolamprotes* spp., *Argyresthia* spp., *Argyrogramma* spp., *Argyroploce* spp., *Argyrotaenia* spp., *Arotrophora* spp., *Ascotis* spp., *Aspidiotus* spp., *Aspilapteryx* spp., *Asthenoptycha* spp., *Aterpia* spp., *Athetis* spp., *Atomaria* spp., *Atomaria linearis*, *Atta* spp., *Atypha* spp., *Autographa* spp., *Axylia* spp., *Bactra* spp., *Barbara* spp., *Batrachedra* spp., *Battaristis* spp., *Bembecia* spp., *Bemisia* spp., *Bemisia tabaci*, *Bibio* spp., *Bibio hortulanis*, *Bisigna* spp., *Blastesthia* spp., *Blatta* spp., *Blatella* spp., *Blepharosis* spp., *Bleptina* spp., *Boarmia* spp., *Bombyx* spp., *Bomolocha* spp., *Boophilus* spp., *Brachmia* spp., *Bradina* spp., *Brevipalpus* spp., *Brithys* spp., *Bryobia* spp., *Bryobia praetiosa*, *Bryotropha* spp., *Bupalus* spp., *Busseola* spp., *Busseola fusca*, *Cabera* spp., *Cacoecimorpha* spp., *Cadra* spp., *Cadra cautella*, *Caenurgina* spp., *Calipitrimerus* spp., *Callierges* spp., *Callophpora* spp., *Callophpora erythrocephala*, *Calophasia* spp., *Caloptilia* spp., *Calybites* spp., *Capnoptycha* spp., *Capua* spp., *Caradrina* spp., *Caripeta* spp., *Carmenta* spp., *Carposina* spp., *Carposina nipponensis*, *Catamacta* spp., *Catelaphris* spp., *Catoptria* spp., *Caustoloma* spp., *Celaena* spp., *Celypha* spp., *Cenopis* spp., *Cephus* spp., *Ceramica* spp., *Cerapteryx* spp., *Ceratitis* spp, *Ceratophyllus* spp., *Ceroplaster* spp., *Chaetocnema* spp., *Chaetocnema tibialis*, *Chamaesphecia* spp., *Charanvca* spp., *Cheimophila* spp., *Chersotis* spp., *Chiasmia* spp., *Chilo* spp., *Chionodes* spp., *Chorioptes* spp., *Choristoneura* spp., *Chrysaspidia* spp., *Chrysodeixis* spp., *Chrysomya* spp., *Chrysomphalus* spp., *Chrysomphalus dictyospermi*, *Chrysomphalus aonidium*, *Chrysoteuchia* spp., *Cilix* spp., *Cimex* spp., *Clysia* spp., *Clysia ambiguelia*, *Clepsis* spp., *Cnaemidophorus* spp., *Cnaphalocrocis* spp., *Cnephasia* spp., *Coccus* spp., *Coccus hesperidum*, *Cochylis* spp., *Coleophora* spp., *Colotois* spp., *Commophila* spp., *Conistra* spp., *Conopomorpha* spp., *Corcyra* spp., *Comutiplusia* spp., *Cosmia* spp., *Cosmopolites* spp., *Cosmopterix* spp., *Cossus* spp., *Costaeonvexa* spp., *Crambus* spp., *Creatonotos* spp., *Crocidolomia* spp., *Crocidolomia binotalis*, *Croesia* spp., *Crymodes* spp., *Cryptaspasma* spp., *Cryptoblabes* spp., *Cryptocala* spp., *Cryptophlebia* spp., *Cryptophlebia leucotreta*, *Cryptoptila* spp., *Ctenopseustis* spp., *Ctenocephalides* spp., *Cucullia* spp., *Curcullo* spp., *Culex* spp., *Cuterebra* spp., *Cydia* spp., *Cydia pomonella*, *Cymbalophora* spp., *Dactylethra* spp., *Dacus* spp., *Dadica* spp., *Damalinea* spp., *Dasychira* spp., *Decadarchis* spp., *Decodes* spp., *Deilephila* spp., *Deltodes* spp., *Dendrolimus* spp., *Depressaria* spp., *Dermestes* spp., *Dermanyssus* spp., *Dermanyssus gallinae*, *Diabrotica* spp., *Diachrysia* spp., *Diaphania* spp., *Diarsia* spp., *Diasemia* spp., *Diatraea* spp., *Diceratura* spp., *Dichomeris* spp., *Dichrocrocis* spp., *Dichrorampha* spp., *Dicycla* spp., *Dioryctria* spp., *Diparopsis* spp., *Diparopsis castanea*, *Dipleurina* spp., *Diprion* spp., *Diprionidae*, *Discestra* spp., *Distantiella* spp., *Distantiella theobroma*, *Ditula* spp., *Diurnea* spp., *Doratopteryx* spp., *Drepana* spp., *Drosphila* spp., *Drosphila melanogaster*, *Dysauxes* spp., *Dysdercus* spp., *Dysstroma* spp., *Eana* spp., *Earias* spp., *Ecclitica* spp., *Ecdytolopha* spp., *Ecpyrrhorrhoe* spp., *Ectomyelois* spp., *Eetropis* spp., *Egira* spp., *Elasmopalpus* spp., *Emmelia* spp., *mpoasca* spp., *Empyreuma* spp., *Enargia* spp., *Enarmonia* spp., *Endopiza* spp., *Endothenia* spp., *Endotricha* spp., *Eoreuma* spp., *Eotetranychus* spp., *Eotetranychus carpini*, *Epagoge* spp., *Epelis* spp., *Ephestia* spp., *Ephestiodes* spp., *Epiblema* spp., *Epiehoristodes* spp., *Epinotia* spp., *Epiphyas* spp., *Epiplema* spp., *Epipsestis* spp., *Epirrhoe* spp., *Episimus* spp., *Epitymbia* spp., *Epllachna* spp., *Erannis* spp., *Erastria* spp., *Eremnus* spp., *Ereunetis* spp., *Eriophyes* spp., *Eriosoma* spp., *Eriosoma lanigerum*, *Erythroneura* spp., *Estigmene* spp., *Ethmia* spp., *Etiella* spp., *Euagrotis* spp., *Eucosma* spp., *Euehlaena* spp., *Euelidia* spp., *Eueosma* spp., *Euchistus* spp., *Eucosmomorpha* spp., *Eudonia* spp., *Eufidonia* spp., *Euhyponomeutoides* spp., *Eulepitodes* spp., *Eulia* spp., *Eulithis* spp., *Eupithecia* spp., *Euplexia* spp., *Eupoecilia* spp., *Eupoecilia ambiguella*, *Euproctis* spp., *Eupsilia* spp., *Eurhodope* spp., *Eurois* spp., *Eurygaster* spp., *Eurythmia* spp., *Eustrotia* spp., *Euxoa* spp., *Euzophera* spp., *Evergestis* spp., *Evippe* spp., *Exartema* spp., *Fannia* spp., *Faronta* spp., *Feltia* spp., *Filatima* spp., *Fishia* spp., *Frankliniella* spp., *Fumibotys* spp., *Gaesa* spp., *Gasgardia* spp., *Gastrophilus* spp., *Gelechia* spp., *Gilpinia* spp., *Gilpinia polytoma*, *Glossina* spp., *Glyphipterix* spp., *Glyphodes* spp., *Gnorimoschemini* spp., *Gonodonta* spp., *Gortyna* spp., *Gracillaria* spp., *Graphania* spp., *Grapholita* spp., *Grapholitha* spp., *Gravitarmata* spp., *Gretchena* spp., *Griselda* spp., *Gryllotalpa* spp., *Gynaephora* spp., *Gypsonoma* spp., *Hada* spp., *Haematopinus* spp., *Halisidota* spp., *Harpipteryx* spp., *Harrisina* spp., *Hedya* spp., *Helicoverpa* spp., *Heliophobus* spp.,

*Heliothis* spp., *Hellula* spp., *Helotropa* spp., *Hemaris* spp., *Hercinothrips* spp., *Herculia* spp., *Hermonassa* spp., *Heterogenea* spp., *Holomelina* spp., *Homadaula* spp., *Homoeosoma* spp., *Homogiaea* spp., *Homohadena* spp., *Homona* spp., *Homonopsis* spp., *Hoplocampa* spp., *Hoplodrina* spp., *Hoshinoa* spp., *Hxalomma* spp., *Hydraecia* spp., *Hydriomena* spp., *Hyles* spp., *Hyloicus* spp., *Hypagyrtis* spp., *Hypatima* spp., *Hyphantria* spp., *Hyphantria cunea, Hypocala* spp., *Hypocoena* spp., *Hypodema* spp., *Hyppobosca* spp., *Hypsipyla* spp., *Hyssia* spp., *Hysterosia* spp., *Idaea* spp., *Idia* spp., *Ipimorpha* spp., *Isia* spp., *Isochorista* spp., *Isophrictis* spp., *Isopolia* spp., *Isotrias* spp., *Ixodes* spp., *Itame* spp., *Jodia* spp., *Jodis* spp., *Kawabea* spp., *Keiferia* spp., *Keiferia lycopersicella, Labdia* spp., *Lacinipolia* spp., *Lambdina* spp., *Lamprothritpa* spp., *Laodelphax* spp., *Lasius* spp., *Laspeyresia* spp., *Leptinotarsa* spp., *Leptinotarsa decemlineata, Leptocorisa* spp., *Leptostales* spp., *Lecanium* spp., *Lecanium corni, Lepidosaphes* spp., *Lepisma* spp., *Lepisma saccharina, Lesmone* spp., *Leucania* spp., *Leucinodes* spp., *Leucophaea* spp., *Leucophaea maderae, Leucoptera* spp., *Leucoptera scitelia, Linognathus* spp., *Liposcelis* spp., *Lissorhoptrus* spp., *Lithacodia* spp., *Lithocolletis* spp., *Lithomoia* spp., *Lithophane* spp., *Lixodessa* spp., *Lobesia* spp., *Lobesia botrana, Lobophora* spp., *Locusta* spp., *Lomanaltes* spp., *Lomographa* spp., *Loxagrotis* spp., *Loxostege* spp., *Lucilia* spp., *Lymantria* spp., *Lymnaecia* spp., *Lyonetia* spp., *Lyriomyza* spp., *Macdonnoughia* spp., *Macrauzata* spp., *Macronoctua* spp., *Macrosiphus* spp., *Malacosoma* spp., *Maliarpha* spp., *Mamestra* spp., *Mamestra brassicae, Manduca* spp., *Manduca sexta, Marasmia* spp., *Margaritia* spp., *Matratinea* spp., *Matsumuraeses* spp., *Melanagromyza* spp., *Melipotes* spp., *Melissopus* spp., *Melittia* spp., *Melolontha* spp., *Meristis* spp., *Meritastis* spp., *Merophyas* spp., *Mesapamea* spp., *Mesogona* spp., *Mesoleuca* spp., *Metanema* spp., *Metendothenia* spp., *Metzneria* spp., *Micardia* spp., *Microcorses* spp., *Microleon* spp., *Mnesictena* spp., *Mocis* spp., *Monima* spp., *Monochroa* spp., *Monomorium* spp., *Monomorium pharaonis, Monopsis* spp., *Morrisonia* spp., *Musca* spp., *Mutuuraia* spp., *Myelois* spp., *Mythimna* spp., *Myzus* spp., *Naranga* spp., *Nedra* spp., *Nemapogon* spp., *Neodiprion* spp., *Neosphaleroptera* spp., *Nephelodes* spp., *Nephotettix* spp., *Nezara* spp., *Nilaparvata* spp., *Niphonympha* spp., *Nippoptilia* spp., *Noctua* spp., *Nola* spp., *Notocelia* spp., *Notodonta* spp., *Nudaurelia* spp., *Ochropleura* spp., *Ocnerostoma* spp., *Oestrus* spp., *Olethreutes* spp., *Oligia* spp., *Olindia* spp., *Olygonychus* spp., *Olygonychus gallinae, Oncocnemis* spp., *Operophtera* spp., *Ophisma* spp., *Opogona* spp., *Oraesia* spp., *Orniodoros* spp., *Orgyia* spp., *Oria* spp., *Orseolia* spp., *Orthodes* spp., *Orthogonia* spp., *Orthosia* spp., *Oryzaephilus* spp., *Oscinella* spp., *Oscinella frit, Osminia* spp., *Ostrinia* spp., *Ostrinia nubilalis, Otiorhynchus* spp., *Ourapteryx* spp., *Pachetra* spp., *Pachysphinx* spp., *Pagyda* spp., *Paleacrita* spp., *Paliga* spp., *Palthis* spp., *Pammene* spp., *Pandemis* spp., *Panemeria* spp., *Panolis* spp., *Panolis flammea, Panonychus* spp., *Parargyresthia* spp., *Paradiarsia* spp., *Paralobesia* spp., *Paranthrene* spp., *Parapandemis* spp., *Parapediasia* spp., *Parastichtis* spp., *Parasyndemis* spp., *Paratoria* spp., *Pareromeme* spp., *Pectinophora* spp., *Pectinophora gossypiella, Pediculus* spp., *Pegomyia* spp., *Pegomyia hyoscyami, Pelochrista* spp., *Pennisetia* spp., *Penstemonia* spp., *Pemphigus* spp., *Peribatodes* spp., *Peridroma* spp., *Perileucoptera* spp., *Periplaneta* spp., *Perizoma* spp., *Petrova* spp., *Pexicopia* spp., *Phalonia* spp., *Phalonidia* spp., *Phaneta* spp., *Phlyctaenia* spp., *Phlyctinus* spp., *Phorbia* spp., *Phragmatobia* spp., *Phricanthes* spp., *Phthorimaea* spp., *Phthorimaea operculella, Phyllocnistis* spp., *Phyllocoptruta* spp., *Phyllocoptruta oleivora, Phyllonorycter* spp., *Phyllophila* spp., *Phylloxera* spp., *Pieris* spp., *Pieris rapae, Piesma* spp., *Planococus* spp., *Planotortrix* spp., *Platyedra* spp., *Platynota* spp., *Platyptilia* spp., *Platysenta* spp., *Plodia* spp., *Plusia* spp., *Plutella* spp., *Plutella xylostella, Podosesia* spp., *Polia* spp., *Popillia*spp., *Polymixis* spp., *Polyphagotarsonemus* spp., *Polyphagotarsonemus latus, Prays* spp., *Prionoxystus* spp., *Probole* spp., *Proceras* spp., *Prochoerodes* spp., *Proeulia* spp., *Proschistis* spp., *Proselena* spp., *Proserpinus* spp., *Protagrotis* spp., *Proteoteras* spp., *Protobathra* spp., *Protoschinia* spp., *Pselnophorus* spp., *Pseudaletia* spp., *Pseudanthonomus* spp., *Pseudaternelia* spp., *Pseudaulacaspis* spp., *Pseudexentera* spp., *Pseudococus* spp., *Pseudohermenias* spp., *Pseudoplusia* spp., *Psoroptes* spp., *Psylla* spp., *Psylliodes* spp., *Pterophorus* spp., *Ptycholoma* spp., *Pulvinaria* spp., *Pulvinaria aethiopica, Pyralis* spp., *Pyrausta* spp., *Pyrgotis* spp., *Pyrreferra* spp., *Pyrrharctia* spp., *Quadraspidiotus* spp., *Rancora* spp., *Raphia* spp., *Reticultermes* spp., *Retinia* spp., *Rhagoletis* spp, *Rhagoletis pomonella, Rhipicephalus* spp., *Rhizoglyphus* spp., *Rhizopertha* spp., *Rhodnius* spp., *Rhophalosiphum* spp., *Rhopobota* spp., *Rhyacia* spp., *Rhyacionia* spp., *Rhynchopacha* spp., *Rhyzosthenes* spp., *Rivula* spp., *Rondotia* spp., *Rusidrina* spp., *Rynchaglaea* spp., *Sabulodes* spp., *Sahlbergella* spp., *Sahlbergella singularis, Saissetia* spp., *Samia* spp., *Sannina* spp., *Sanninoidea* spp., *Saphoideus* spp., *Sarcoptes* spp., *Sathrobrota* spp., *Scarabeidae, Sceliodes* spp., *Schinia* spp., *Schistocerca* spp., *Schizaphis* spp., *Schizura* spp., *Schreckensteinia* spp., *Sciara* spp., *Scirpophaga* spp., *Scirthrips auranti, Scoparia* spp., *Scopula* spp., *Scotia* spp., *Scotinophara* spp., *Scotogramma* spp., *Scrobipalpa* spp., *Scrobipalpopsis* spp., *Semiothisa* spp., *Sereda* spp., *Sesamia*spp., *Sesia* spp., *Sicya* spp., *Sideridis* spp., *Simyra* spp., *Sineugraphe* spp., *Sitochroa* spp., *Sitobion* spp., *Sitophilus* spp., *Sitotroga* spp., *Solenopsis* spp., *Smerinthus* spp., *Sophronia* spp., *Spaelotis* spp., *Spargaloma* spp., *Sparganothis* spp., *Spatalistis* spp., *Sperchia* spp., *Sphecia* spp., *Sphinx* spp., *Spilonota* spp., *Spodoptera* spp., *Spodoptera littoralis, Stagmatophora* spp., *Staphylinochrous* spp., *Stathmopoda* spp., *Stenodes* spp., *Sterrha* spp., *Stomoxys* spp., *Strophedra* spp., *Sunira* spp., *Sutyna* spp., *Swammerdamia* spp., *Syllomatia* spp., *Sympistis* spp., *Synanthedon* spp., *Synaxis* spp., *Syncopacma* spp., *Syndemis* spp., *Syngrapha* spp., *Synthomeida* spp., *Tabanus* spp., *Taeniarchis* spp., *Taeniothrips* spp., *Tannia* spp., *Tarsonemus* spp., *Tegulifera* spp., *Tehama* spp., *Teleiodes* spp., *Telorta* spp., *Tenebrio* spp., *Tephrina* spp., *Teratoglaea* spp., *Terricula* spp., *Tethea* spp., *Tetranychus* spp., *Thalpophila* spp., *Thaumetopoea* spp., *Thiodia* spp., *Thrips* spp., *Thrips* palmi, *Thrips tabaci, Thyridopteryx* spp., *Thyris* spp., *Tineola* spp., *Tipula* spp., *Tortricidia* spp., *Tortrix* spp., *Trachea* spp., *Trialeurodes* spp., *Trialeurodes vaporariorum, Triatoma* spp., *Triaxomera* spp., *Tribolium* spp., *Tricodectes* spp., *Trichoplusia* spp., *Trichoplusia ni, Trichoptilus* spp., *Trioza* spp., *Trioza erytreae, Triphaenia* spp., *Triphosa* spp., *Trogoderma* spp., *Tyria* spp., *Udea* spp., *Unaspis* spp., *Unaspis citri, Utetheisa* spp., *Valeriodes* spp., *Vespa* spp., *Vespamima* spp., *Vitacea* spp., *Vitula* spp., *Witlesia* spp., *Xanthia* spp., *Xanthorhoe* spp., *Xanthotype* spp., *Xenomicta* spp., *Xenopsylla* spp., *Xenopsylla cheopsis, Xestia* spp., *Xylena* spp., *Xylomyges* spp., *Xyrosaris* spp., *Yponomeuta* spp., *Ypsolopha* spp, *Zale* spp., *Zanclognathus* spp., *Zeiraphera* spp., *Zenodoxus* spp., *Zeuzera* spp., *Zygaena* spp., It is also possible to control pests of the class Nematoda using the compounds according to the invention. Such pests include, for example, root knot nematodes, cyst-forming nematodes and also stem and leaf nematodes;

especially of *Heterodera* spp., e.g. *Heterodera schachtii*, *Heterodora avenae* and *Heterodora trifolii*; *Globodera* spp., e.g. *Globodera rostochiensis*; *Meloidogyne* spp., e.g. *Meloidogyne incognita* and *Meloidogyne javanica*; *Radopholus* spp., e.g. *Radopholus similis*; *Pratylenchus*, e.g. *Pratylenchus neglectans* and *Pratylenchus penetrans*; *Tylenchulus*, e.g. *Tylenchulus semipenetrans*; *Longidorus*, *Trichodorus*, *Xiphinema*, *Ditylenchus*, *Apheenchoides* and *Anguina*; especially *Meloidogyne*, e.g. *Meloidogyne incognita*, and *Heterodera*, e.g. *Heterodera* glycines.

An especially important aspect of the present invention is the use of the compounds of formula (I) according to the invention in the protection of plants against parasitic feeding pests.

The action of the compounds according to the invention and the compositions comprising them against animal pests can be significantly broadened and adapted to the given circumstances by the addition of other insecticides, acaricides or nematicides. Suitable additives include, for example, representatives of the following classes of active ingredient: organophosphorus compounds, nitrophenols and derivatives, formamidines, ureas, carbamates, pyrethroids, chlorinated hydrocarbons, neonicotinoids and *Bacillus thuringiensis* preparations.

Examples of especially suitable mixing partners include: azamethiphos; chlorfenvinphos; cypermethrin, cypermethrin high-cis; cyromazine; diafenthiuron; diazinon; dichlorvos; dicrotophos; dicyclanil; fenoxycarb; fluazuron; furathiocarb; isazofos; iodfenphos; kinoprene; lufenuron; methacriphos; methidathion; monocrotophos; phosphamidon; profenofos; diofenolan; a compound obtainable from the *Bacillus thuringiensis* strain GC91 or from strain NCTC11821; pymetrozine; bromopropylate; methoprene; disulfoton; quinalphos; tau-fluvalinate; thiocyclam; thiometon; aldicarb; azinphos-methyl; benfuracarb; bifenthrin; buprofezin; carbofuran; dibutylaminothio; cartap; chlorfluazuron; chlorpyrifos; clothianidin; cyfluthrin; lambda-cyhalothrin; alpha-cypermethrin; zeta-cypermethrin; deltamethrin; diflubenzuron; endosulfan; ethiofencarb; fenitrothion; fenobucarb; fenvalerate; formothion; methiocarb; heptenophos; imidacloprid; isoprocarb; methamidophos; methomyl; mevinphos; parathion; parathion-methyl; phosalone; pirimicarb; propoxur; teflubenzuron; terbufos; triazamate; fenobucarb; tebufenozide; fipronil; beta-cyfluthrin; silafluofen; fenpyroximate; pyridaben; pyridalyl; fenazaquin; pyriproxyfen; pyrimidifen; nitenpyram; acetamiprid; emamectin; emamectin-benzoate; spinosad; a plant extract that is active against insects; a preparation that comprises nematodes and is active against insects; a preparation obtainable from *Bacillus subtilis*; a preparation that comprises fungi and is active against insects; a preparation that comprises viruses and is active against insects; chlorfenapyr; acephate; acrinathrin; alanycarb; alphamethrin; amitraz; AZ 60541; azinphos A; azinphos M; azocyclotin; bendiocarb; bensultap; beta-cyfluthrin; brofenprox; bromophos A; bufencarb; butocarboxin; butylpyridaben; cadusafos; carbaryl; carbophenothion; chloethocarb; chlorethoxyfos; chlormephos; cis-resmethrin; clocythrin; clofentezine; cyanophos; cyclothothrin; cyhexatin; demeton M; demeton S; demeton-S-methyl; dichlofenthion; dicliphos; diethion; dimethoate; dimethylvinphos; dinotefuran; dioxathion; edifenphos; esfenvalerate; ethion; ethofenprox; ethoprophos; etrimphos; fenamiphos; fenbutatin oxide; fenothiocarb; fenpropathrin; fenpyrad; fenthion; fluazinam; flucycloxuron; flucythrinate; flufenoxuron; flufen-prox; fonophos; fosthiazate; fubfenprox; HCH; hexaflumuron; hexythiazox; flonicamid; iprobenfos; isofenphos; isoxathion; ivermectin; malathion; mecarbam; mesulfenphos; metaldehyde; metolcarb; milbemectin; moxidectin; naled; NC 184; nithiazine; omethoate; oxamyl; oxydemethon M; oxydeprofos; permethrin; phenthoate; phorate; phosmet; phoxim; pirimiphos M; pirimiphos E; promecarb; propaphos; prothiofos; prothoate; pyrachlophos; pyradaphenthion; pyresmethrin; pyrethrum; tebufenozide; salithion; sebufos; sulfotep; sulprofos; tebufenpyrad; tebupirimphos; tefluthrin; temephos; terbam; tetrachlorvinphos; thiacloprid; thiafenox; thiamethoxam; thiodicarb; thiofanox; thionazin; thuringiensin; tralomethrin; triarathene; triazophos; triazuron; trichlorfon; triflumuron; trimethacarb; vamidothion; xylylcarb; etoxazole; zetamethrin; indoxacarb; methoxyfenozide; bifenazate; XMC (3,5-xylyl methylcarbamate); or the fungus pathogen *Metarhizium anisopliae*.

The compounds according to the invention can be used to control, i.e. to inhibit or destroy, pests of the mentioned type occurring on plants, especially on useful plants and ornamentals in agriculture, in horticulture and in forestry, or on parts of such plants, such as the fruits, blossoms, leaves, stems, tubers or roots, while in some cases plant parts that grow later are still protected against those pests.

Target crops include especially cereals, such as wheat, barley, rye, oats, rice, maize and sorghum; beet, such as sugar beet and fodder beet; fruit, e.g. pomes, stone fruit and soft fruit, such as apples, pears, plums, peaches, almonds, cherries and berries, e.g. strawberries, raspberries and blackberries; leguminous plants, such as beans, lentils, peas and soybeans; oil plants, such as rape, mustard, poppy, olives, sunflowers, coconut, castor oil, cocoa and groundnuts; cucurbitaceae, such as marrows, cucumbers and melons; fibre plants, such as cotton, flax, hemp and jute; citrus fruits, such as oranges, lemons, grapefruit and mandarins; vegetables, such as spinach, lettuce, asparagus, cabbages, carrots, onions, tomatoes, potatoes and paprika; lauraceae, such as avocado, cinnamon and camphor; and tobacco, nuts, coffee, aubergines, sugar cane, tea, pepper, vines, hops, bananas, natural rubber plants and ornamentals.

Further areas of use of the compounds according to the invention are the protection of stored goods and storerooms and the protection of raw materials, and also in the hygiene sector, especially the protection of domestic animals and productive livestock against pests of the mentioned type, more especially the protection of domestic animals, especially cats and dogs, from infestation by fleas, ticks and nematodes.

The invention therefore relates also to pesticidal compositions, such as emulsifiable concentrates, suspension concentrates, directly sprayable or dilutable solutions, spreadable pastes, dilute emulsions, wettable powders, soluble powders, dispersible powders, wettable powders, dusts, granules and encapsulations of polymer substances, that comprise at least one of the compounds according to the invention, the choice of formulation being made in accordance with the intended objectives and the prevailing circumstances.

The active ingredient is used in those compositions in pure form, a solid active ingredient, for example, in a specific particle size, or preferably together with at least one of the adjuvants customary in formulation technology, such as extenders, e.g. solvents or solid carriers, or surface-active compounds (surfactants). In the area of parasite control in humans, domestic animals, productive livestock and pets it will be self-evident that only physiologically tolerable additives are used.

Solvents are, for example: non-hydrogenated or partly hydrogenated aromatic hydrocarbons, preferably fractions $C_8$ to $C_{12}$ of alkylbenzenes, such as xylene mixtures, alkylated naphthalenes or tetrahydronaphthalene, aliphatic or cycloaliphatic hydrocarbons, such as paraffins or cyclohexane, alcohols, such as ethanol, propanol or butanol, glycols and ethers and esters thereof, such as propylene glycol, dipropylene glycol ether, ethylene glycol or ethylene glycol monomethyl or -ethyl ether, ketones, such as cyclohexanone, isophorone or diacetone alcohol, strongly polar solvents, such as N-methylpyrrolid-2-one, dimethyl sulfoxide or N,N-dimethylformamide, water, non-epoxidized or epoxidized plant oils, such as non-epoxidized or epoxidized rapeseed, castor, coconut or soya oil, and silicone oils.

The solid carriers used, for example for dusts and dispersible powders, are as a rule natural rock powders, such as calcite, talc, kaolin, montmorillonite or attapulgite. Highly disperse silicic acids or highly disperse absorbent polymers can also be added to improve the physical properties. Granular adsorptive granule carriers are porous types, such as pumice, crushed brick, sepiolite or bentonite, and non-sorbent carrier materials are calcite or sand. A large number of granular materials of inorganic or organic nature can furthermore be used, in particular dolomite or comminuted plant residues.

Surface-active compounds are, depending on the nature of the active compound to be formulated, nonionic, cationic and/or anionic surfactants or surfactant mixtures with good emulsifying, dispersing and wetting properties. The surfactants listed below are to be regarded only as examples; many other surfactants which are customary in formulation technology and are suitable according to the invention are described in the relevant literature.

Nonionic surfactants are, in particular, polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl radical of the alkylphenols. Substances which are furthermore suitable are water-soluble polyethylene oxide adducts, containing 20 to 250 ethylene glycol ether and 10 to 100 propylene glycol ether groups, on propylene glycol, ethylene diaminopolypropylene glycol and alkyl polypropylene glycol having 1 to 10 carbon atoms in the alkyl chain. The compounds mentioned usually contain 1 to 5 ethylene glycol units per propylene glycol unit. Examples are nonylphenol-polyethoxyethanols, castor oil polyglycol ethers, polypropylene-polyethylene oxide adducts, tributylphenoxypoly-ethoxyethanol, polyethylene glycol and octylphenoxypolyethoxyethanol. Other substances are fatty acid esters of polyoxyethylene sorbitan, such as polyoxyethylene sorbitan trioleate.

The cationic surfactants are, in particular, quaternary ammonium salts which contain, as substituents, at least one alkyl radical having 8 to 22 C atoms and, as further substituents, lower, non-halogenated or halogenated alkyl, benzyl or lower hydroxyalkyl radicals. The salts are preferably in the form of halides, methyl-sulfates or ethyl-sulfates. Examples are stearyltrimethyl-ammonium chloride and benzyl-di-(2-chloroethyl)-ethyl-ammonium bromide.

Suitable anionic surfactants can be both water-soluble soaps and water-soluble synthetic surface-active compounds. Suitable soaps are the alkali metal, alkaline earth metal and substituted or unsubstituted ammonium salts of higher fatty acids ($C_{10}$-$C_{22}$), such as the sodium or potassium salts of oleic or stearic acid, or of naturally occurring fatty acid mixtures, which can be obtained, for example, from coconut oil or tall oil; and furthermore also the fatty acid methyltaurine salts. However, synthetic surfactants are more frequently used, in particular fatty sulfonates, fatty sulfates, sulfonated benzimidazole derivatives or alkylarylsulfonates. The fatty sulfonates and sulfates are as a rule in the form of alkali metal, alkaline earth metal or substituted or unsubstituted-ammonium salts and in general have an alkyl radical of 8 to 22 C atoms, alkyl also including the alkyl moiety of acyl radicals; examples are the sodium or calcium salt of ligninsulfonic acid, of dodecylsulfuric acid ester or of a fatty alcohol sulfate mixture prepared from naturally occurring fatty acids. These also include the salts of sulfuric acid esters and sulfonic acids of fatty alcoholethylene oxide adducts. The sulfonated benzimidazole derivatives preferably contain 2 sulfonic acid groups and a fatty acid radical having about 8 to 22 C atoms. Alkylarylsulfonates are, for example, the sodium, calcium or triethanolammonium salts of dodecylbenzenesulfonic acid, of dibutylnaphthalenesulfonic acid or of a naphthalenesulfonic acid-formaldehyde condensation product. Corresponding phosphates, such as salts of the phosphoric acid ester of a p-nonylphenol-(4-14)-ethylene oxide adduct or phospholipids, can further also be used.

The compositions as a rule comprise 0.1 to 99%, in particular 0.1 to 95%, of active compound and 1 to 99.9%, in particular 5 to 99.9%, of—at least—one solid or liquid auxiliary, it being possible as a rule for 0 to 25%, in particular 0.1 to 20%, of the composition to be surfactants (% is in each case percent by weight). While concentrated compositions are more preferred as commercial goods, the end user as a rule uses dilute compositions which comprise considerably lower concentrations of active compound. Preferred compositions are composed, in particular, as follows (%=percent by weight):

Emulsifiable Concentrates:

| | |
|---|---|
| active ingredient: | 1 to 90%, preferably 5 to 20% |
| surfactant: | 1 to 30%, preferably 10 to 20% |
| solvent: | 5 to 98%, preferably 70 to 85% |

Dusts:

| | |
|---|---|
| active ingredient: | 0.1 to 10%, preferably 0.1 to 1% |
| solid carrier: | 99.9 to 90%, preferably 99.9 to 99% |

Suspension Concentrates:

| | |
|---|---|
| active ingredient: | 5 to 75%, preferably 10 to 50% |
| water: | 94 to 24%, preferably 88 to 30% |
| surfactant: | 1 to 40%, preferably 2 to 30% |

Wettable Powders:

| active ingredient: | 0.5 to 90%, preferably 1 to 80% |
| --- | --- |
| surfactant: | 0.5 to 20%, preferably 1 to 15% |
| solid carrier: | 5 to 99%, preferably 15 to 98% |

Granules:

| active ingredient: | 0.5 to 30%, preferably 3 to 15% |
| --- | --- |
| solid carrier: | 99.5 to 70%, preferably 97 to 85% |

The compositions according to the invention may also comprise further solid or liquid adjuvants, such as stabilisers, e.g. vegetable oils or epoxidised vegetable oils (e.g. epoxidised coconut oil, rapeseed oil or soybean oil), antifoams, e.g. silicone oil, preservatives, viscosity regulators, binders and/or tackifiers as well as fertilisers or other active ingredients for obtaining special effects, e.g. acaricides, bactericides, fungicides, nematicides, molluscicides or selective herbicides.

The crop protection products according to the invention are prepared in known manner, in the absence of adjuvants, e.g. by grinding, sieving and/or compressing a solid active ingredient or mixture of active ingredients, for example to a certain particle size, and in the presence of at least one adjuvant, for example by intimately mixing and/or grinding the active ingredient or mixture of active ingredients with the adjuvant(s). The invention relates likewise to those processses for the preparation of the compositions according to the invention and to the use of the compounds of formula (I) in the preparation of those compositions.

The invention relates also to the methods of application of the crop protection products, i.e. the methods of controlling pests of the mentioned type, such as spraying, atomising, dusting, coating, dressing, scattering or pouring, which are selected in accordance with the intended objectives and the prevailing circumstances, and to the use of the compositions for controlling pests of the mentioned type. Typical rates of concentration are from 0.1 to 1000 ppm, preferably from 0.1 to 500 ppm, of active ingredient. The rates of application per hectare are generally from 1 to 2000 g of active ingredient per hectare, especially from 10 to 1000 g/ha, preferably from 20 to 600 g/ha, more especially from 20 to 100 g/ha.

A preferred method of application in the area of crop protection is application to the foliage of the plants (foliar application), the frequency and the rate of application being dependent upon the risk of infestation by the pest in question. However, the active ingredient can also penetrate the plants through the roots (systemic action) when the locus of the plants is impregnated with a liquid formulation or when the active ingredient is incorporated in solid form into the locus of the plants, for example into the soil, e.g. in granular form (soil application). In the case of paddy rice crops, such granules may be applied in metered amounts to the flooded rice field.

The crop protection products according to the invention are also suitable for protecting plant propagation material, e.g. seed, such as fruits, tubers or grains, or plant cuttings, against animal pests. The propagation material can be treated with the composition before planting: seed, for example, can be dressed before being sown. The active ingredients according to the invention can also be applied to grains (coating), either by impregnating the seeds in a liquid formulation or by coating them with a solid formulation. The composition can also be applied to the planting site when the propagation material is being planted, for example to the seed furrow during sowing. The invention relates also to such methods of treating plant propagation material and to the plant propagation material so treated.

The following Examples serve to illustrate the invention. They do not limit the invention. Temperatures are given in degrees Celsius; mixing ratios of solvents are given in parts by volume. In the examples, TBDMS is t-butyl-dimethylsilyl

PREPARATION EXAMPLES

Example A2.1

4"-Desoxy-4"-(S)-phtalimidooxy-avermectin $B_1$

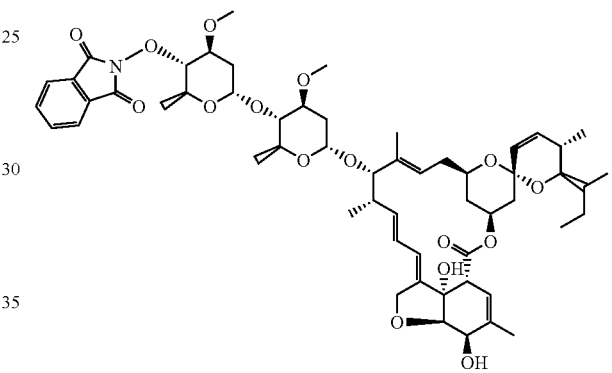

Step A: 1.0 g of 5-OTBDMS-4"-desoxy-avermectin $B_1$-4"-(R)-trifluoromethanesulfonate and 0.44 g of N-hydroxyphtalimide is dissolved in 20 ml acetonitrile. The solution is cooled to 0° C. then 0.2 ml of 1,8-diazabicyclo [5.4.0]undec-7-ene in 2 ml acetonitrile are added dropwise over 15 min. The reaction mixture is stirred at room temperature for 3 hours, diluted with ethyl acetate, washed with saturated ammonium chloride, water and brine. The organic phase is dried over sodium sulfate, and concentrated in vacuo. The residue is purified by flash-chromatography (silica gel hexane/ethyl acetate 8/2) providing 5-OTBDMS-4"-desoxy-4"-(S)-phtalimidooxy-avermectin $B_1$ which is characterized by its mass and NMR spectra.

Step B: To a solution of 0.54 g of 5-OTBDMS-4"-desoxy-4"-(S)-phtalimidooxy-avermectin $B_1$ in 10 ml tetrahydrofuran is added 2 ml of a HF-pyridine solution (consisting of 25 g 70% HF-Pyridin, 27,5 ml tetrahydrofuran and 12,5 ml pyridine), and the mixture is stirred at room temperature for 24 hours, poured into water, extracted with ethyl acetate; the organic phase is washed with saturated sodium bicarbonate, dried over sodium sulfate, and concentrated in vacuo. The residue is purified by flash-chromatography (silica gel hexane/ethyl acetate 6/4) providing 4"-desoxy-4"-(S)-phtalimidooxy-avermectin $B_1$ which is characterized by its mass and NMR spectra.

Example A4.1

4"-Desoxy-4"-(R)-phtalimidooxy-avermectin B$_1$

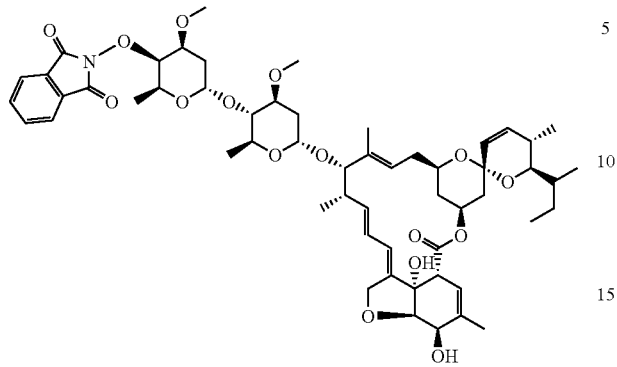

Step A: 1.0 g of 5-OTBDMS-4"-desoxy-avermectin B$_1$-4"-(S)-trifluoromethanesulfonate and 0.44 g of N-hydroxyphtalimide is dissolved in 20 ml acetonitrile. The solution is cooled to 0° C. then 0.2 ml of 1,8-diazabicyclo[5.4.0]undec-7-ene (DBU) in 2 ml acetonitrile are added dropwise over 15 min. The reaction mixture is stirred at room temperature for 3 hours, diluted with ethyl acetate, washed with saturated ammonium chloride, water and brine. The organic phase is dried over sodium sulfate, and concentrated in vacuo. The residue is purified by flash-chromatography (silica gel hexane/ethyl acetate 85/15) providing 5-OTBDMS-4"-desoxy-4"-(R)-phtalimidooxy-avermectin B$_1$ which is characterized by its mass and NMR spectra.

Step B: To a solution of 0.54 g of 5-OTBDMS-4"-desoxy-4"-(R)-phtalimidooxy-avermectin B$_1$ in 10 ml tetrahydrofuran is added 2 ml of a HF-pyridine solution (consisting of 25 g 70% HF-Pyridin, 27.5 ml tetrahydrofuran and 12.5 ml pyridine), and the mixture is stirred at room temperature for 24 hours, poured into water, extracted with ethyl acetate; the organic phase is washed with saturated sodium bicarbonate, dried over sodium sulfate, and concentrated in vacuo. The residue is purified by flash-chromatography (silica gel hexane/ethyl acetate 6/4) providing 4"-desoxy-4"-(R)-phtalimidooxy-avermectin B$_1$ which is characterized by its mass and NMR spectra.

Example A2.2

4"-desoxy-4'-(S)-aminooxy-avermectin B$_1$

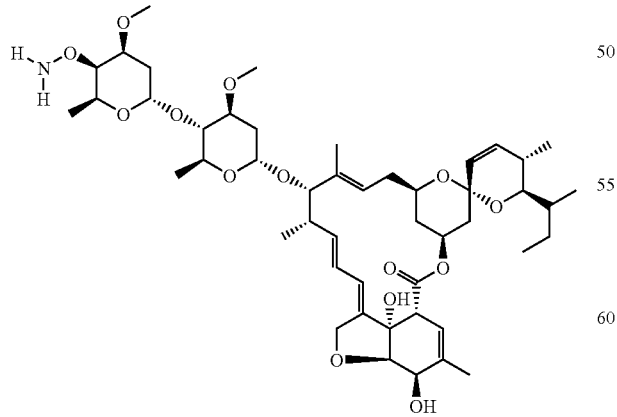

To a solution of 0.4 g of 4"-desoxy-4"-(S)-phtalimidooxy-avermectin B$_1$ (example A2.1) in 7 ml ethanol is added 30 mg of hydrazine monohydrate. The reaction mixture is stirred at room temperature for 1 hour, poured into water, extracted with ethyl acetate, the organic phase is washed with water, saturated sodium bicarbonated, dried over sodium sulfate and concentrated in vacuo, yielding 4"-desoxy-4"-(S)-aminooxy-avermectin B$_1$ which is characterized by its mass and NMR spectra.

Example A4.2

4"-desoxy-4"-(R)-aminooxy-avermectin B$_1$

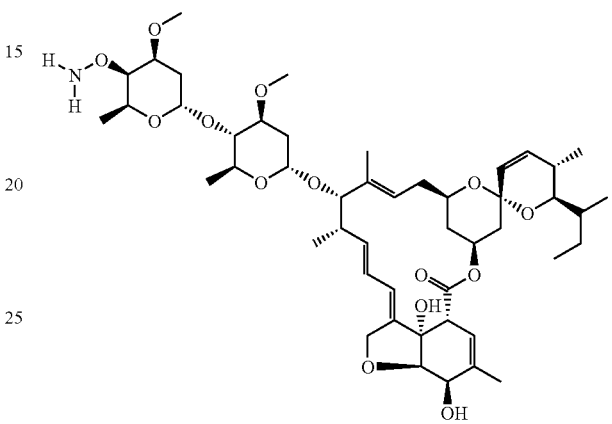

To a solution of 0.15 g of 4"-desoxy-4"-(R)-phtalimidooxy-avermectin B$_1$ (example A2.1) in 5 ml ethanol is added 11 mg of hydrazine monohydrate. The reaction mixture is stirred at room temperature for 1 hour, poured into water, extracted with ethyl acetate; the organic phase is washed with water, saturated sodium bicarbonated, dried over sodium sulfate and concentrated in vacuo, yielding 4"-desoxy-4"-(R)-aminooxy-avermectin B$_1$, which is characterized by its mass and NMR spectra.

Example A1.1

4"-Desoxy-4"-(S)-(ethylideneamino)oxy-avermectin B$_1$

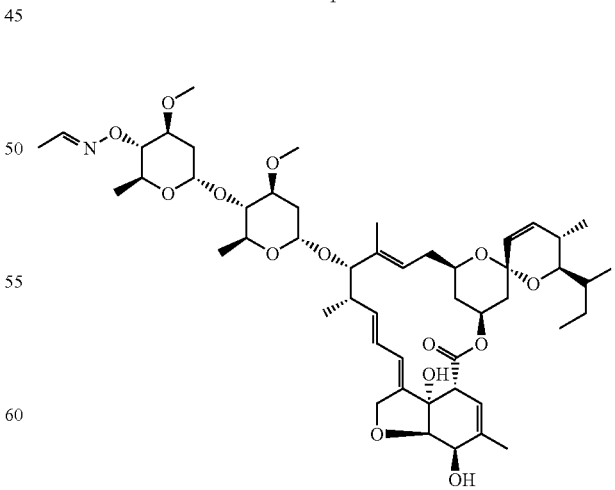

To a solution of 0.1 g of 4"-desoxy-4"-(S)-aminooxy-avermectin B$_1$ (example A2.2) in 5 ml toluene is added 25 mg acetaldehyde. The reaction mixture is stirred at room temperature for 1 hour and concentrated in vacuo, yielding 4"-desoxy-4"-(S)-[(ethylidene)amino]oxy-avermectin $B_1$ which is characterized by its mass and NMR spectra.

Example A1.2

4"-Desoxy-4"-(S)-[(3-hydroxy-ethylidene)amino]oxy-avermectin $B_1$

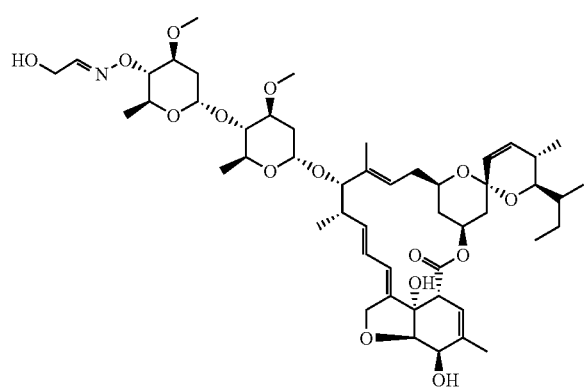

To a solution of 0.1 g of 4"-desoxy-4"-(S)-aminooxy-avermectin $B_1$ (example A2.2) in 5 ml toluene are added 3 mg of pyridinium para-toluene sulfonate and 10 mg of glycolaldehyde. The reaction mixture is stirred at room temperature for 1 hour, poured into water, extracted with ethyl acetate, dried over sodium sulfate and concentrated in vacuo, yielding 4"-desoxy-4"-(S)-[(3-hydroxy-ethylidene)amino]oxy-avermectin $B_1$ which is characterized by its mass and NMR spectra.

Example A1.13

4"-Desoxy-4"-(S)-(cyclopentylideneamino)oxy-avermectin $B_1$

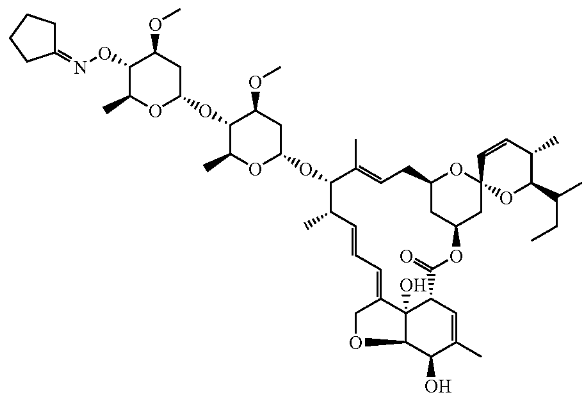

To a solution of 0.1 g of 4"-desoxy-4"-(S)-aminooxy-avermectin $B_1$ (example A2.2) in 5 ml toluene are added 3 mg of pyridinium para-toluene sulfonate and 13 mg of cyclopentanone. The reaction mixture is stirred at room temperature for 1 hour, poured into water, extracted with ethyl acetate, dried over sodium sulfate and concentrated in vacuo, yielding 4"-desoxy-4"-(S)-(cyclopentylideneamino)oxy-avermectin $B_1$ which is characterized by its mass and NMR spectra.

Example A1.16

D-Fructose, 4"-O-(avermectin $B_1$)oxime

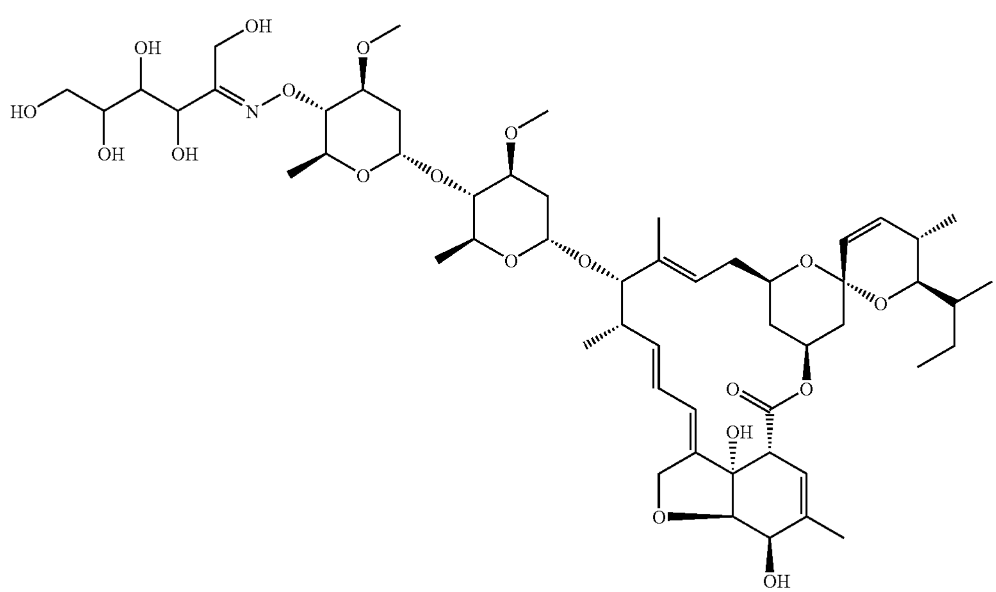

To a solution of 0.1 g of 4"-desoxy-4"-(S)-aminoxy-avermectin B$_1$ (example A2.2) in 5 ml dioxan and 0.05 ml water is added 28 mg of pyridinium para-toluene sulfonate and 202 mg of D-Fructose. The reaction mixture is stirred at room temperature for 24 hours, poured into water, extracted with ethyl acetate, dried over sodium sulfate and concentrated in vacuo, yielding D-Fructose, 4"-O-(avermectin B$_1$)oxime which is characterized by its mass and NMR spectra.

Example A2.3

4"-Desoxy-4"-(S)-(acetylamino)oxy-avermectin B$_1$

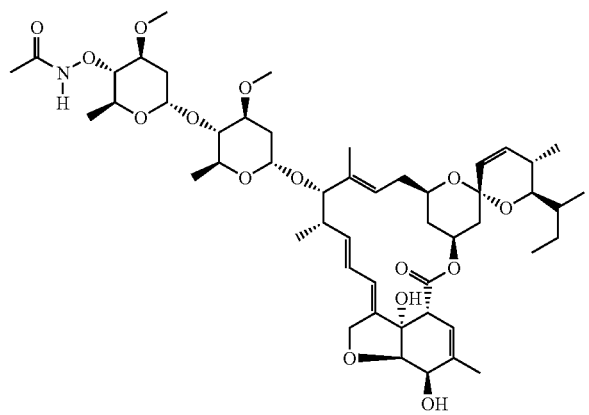

Step A: To a solution of 6 g of 5-OTBDMS-4"-desoxy-4"-(S)-phtalimidooxy-avermectin B$_1$ (example A2.1, step A) in 100 ml ethanol is added 0.39 ml of hydrazine monohydrate. The reaction mixture is stirred at room temperature for 1 hour, poured into water, extracted with ethyl acetate; the organic phase is washed with saturated sodium bicarbonate, dried over sodium sulfate and sulfate and concentrated in vacuo, yielding 5-OTBDMS-4"-desoxy-4"-(S)-aminooxy-avermectin B$_1$.

Step B: To a solution of 0.2 g of 5-OTBDMS-4"-desoxy-4"-(S)-aminooxy-avermectin B$_1$ and 0.03 ml pyridine in 5 ml dichloromethane at 0° C. is added 0.02 ml acetyl chloride. The reaction mixture is stirred at 0° C. for 1 hour, poured into water, extracted with dichloromethane, dried over sodium sulfate and concentrated in vacuo. To a solution of the crude residue in 1.5 ml tetrahydrofuran is is added 0.3 ml of a HF-pyridine solution (consisting of 25 g 70% HF-Pyridine, 27.5 ml tetrahydrofuran and 12.5 ml pyridine), and the mixture is stirred at room temperature for 12 hours, poured into water, extracted with ethyl acetate; the organic phase is washed with saturated sodium bicarbonate, dried over sodium sulfate, and concentrated in vacuo, yielding 4"-desoxy-4"-(S)-(acetylamino)oxy-avermectin B$_1$ which is characterized by its mass and NMR spectra.

Example A2.11

4"-Desoxy-4"-(S)-[(methoxycarbonyl)amino]oxy-avermectin B$_1$

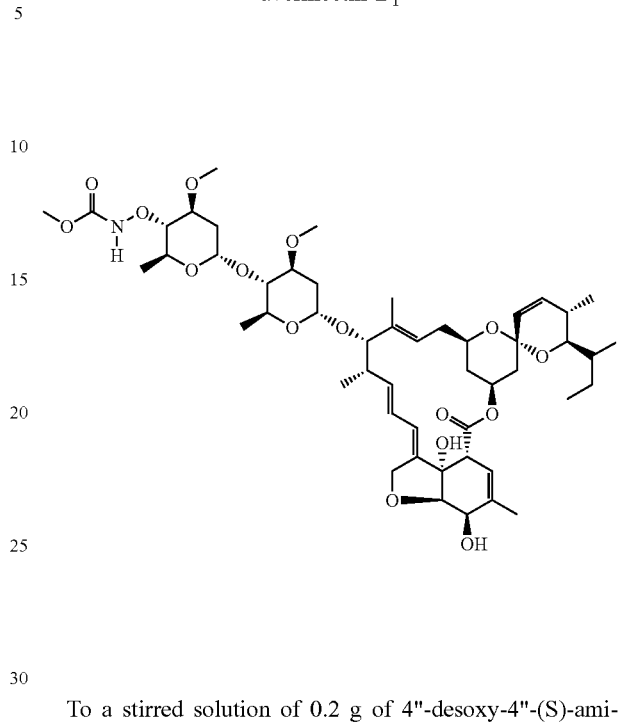

To a stirred solution of 0.2 g of 4"-desoxy-4"-(S)-aminooxy-avermectin B$_1$ (example A2.2) in 3 ml ethyl acetate and 3 ml sodium bicarbonate is added 24 mg of methyl chloroformate. The reaction mixture is stirred at room temperature for 5 hours, diluted with ethyl acetate, washed with brine, dried over sodium sulfate and concentrated in vacuo. The residue is purified by flash-chromatography (silica gel hexane/ethyl acetate 65/35) providing 4"-desoxy-4"-(S)-[(methoxycarbonyl)amino]oxy-avermectin B$_1$ which is characterized by its mass and NMR spectra.

Example A1.17

4"-desoxy-4"-(S)-[(methylidene)amino]oxy-avermectin B$_1$

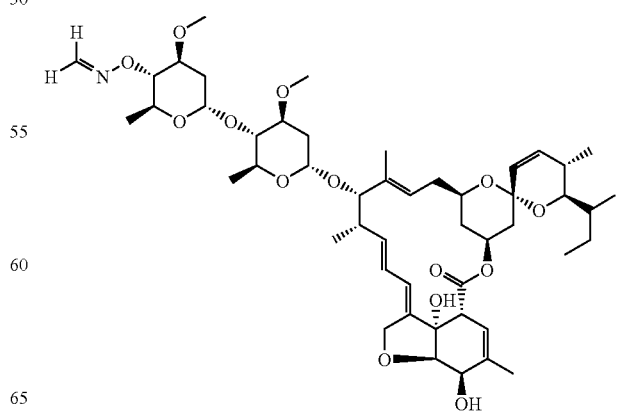

To a solution of 2.62 g of 4"-desoxy-4"-(S)-aminooxy-avermectin $B_1$ (example A2.2) in 25 ml tetrahydrofuran is added 4.84 ml of aqueous formaldehyde (36%). The reaction mixture is stirred at room temperature for 2.5 hours and concentrated in vacuo, yielding 4"-desoxy-4"-(S)-[(methylidene)amino]oxy-avermectin $B_1$ which is characterized by its mass and NMR spectra.

Example A2.13

4"-desoxy-4"-(S)-(methylamino)oxy-avermectin $B_1$

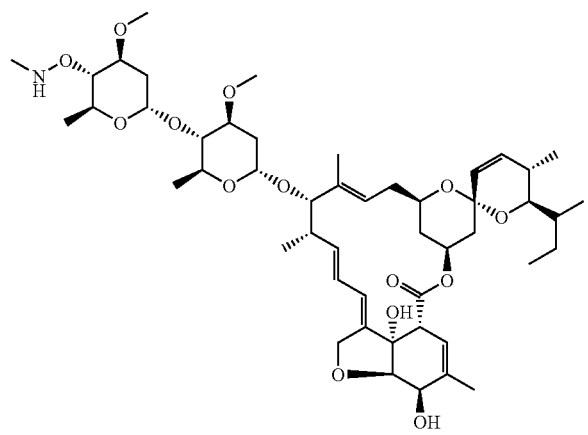

To a solution of 2.78 g of 4"-desoxy-4"-(S)-[(methylidene)amino]oxy-avermectin $B_1$ (example A1.17) in 50 ml toluene is added 25 ml of a solution of diisobutylaluminium-hydride in toluene (1.2 mol/l) under nitrogen. During the addition, the reaction flask is cooled in a water bath, the temperature of the reaction mixture is kept below 25° C. Then the reaction mixture is stirred at room temperature for 3 hours, extracted with ethyl acetate and aqueous sodium tartrate, dried over sodium sulfate and concentrated in vacuo. The residue is purified by chromatography on silica gel with hexane/ethyl acetate, yielding 4"-desoxy-4"-(S)(methylamino)oxy-avermectin B1 which is characterized by its mass and NMR spectra.

Similarly to the preparation examples above it is also possible to prepare the compounds listed in Tables A1 to A8 and Tables 1 to 48. In the Tables, the symbol ⁓⁓⁓ denotes, where necessary, the bond through which the radical in question is attached to the the skeleton.

Since in most cases the compounds are present as mixtures of the avermectin derivatives B1a and B1b, characterization by customary physical data such as melting point or refractive index makes little sense. For this reason, the compounds are characterized by the retention times which are determined in an analysis by HPLC (high performance liquid chromatography). Here, the term B1a refers to the main component in which $R_1$ is sec-butyl, with a content of usually more than 80%. B1b denotes the minor component in which $R_1$ is isopropyl. Where two retention times are given for the B1a or the B1b derivative or both the compounds are mixtures of diastereomers which can be separated chromatographically. In the case of compounds where a retention time is given only in column B1a or only in column B1b, the pure B1a or B1b component, respectively, can be obtained during work-up. The correct structures of the B1a and B1b components are assigned by mass spectrometry.

The following method is used for HPLC analysis:

| HPLC gradient conditions | | | |
| --- | --- | --- | --- |
| Solvent A: | 0.01% of trifluoroacetic acid in $H_2O$ | | |
| Solvent B: | 0.01% of trifluoroacetic acid in $CH_3CN$ | | |
| Time [min] | A [%] | B [%] | Flow rate [µl/min] |
| 0 | 80 | 20 | 500 |
| 0.1 | 50 | 50 | 500 |
| 10 | 5 | 95 | 500 |
| 15 | 0 | 100 | 500 |
| 17 | 0 | 100 | 500 |
| 17.1 | 80 | 20 | 500 |
| 22 | 80 | 20 | 500 |
| Type of column | YMC-Pack ODS-AQ | | |
| Column length | 125 mm | | |
| Internal diameter of column: | 2 mm | | |
| Temperature | 40° C. | | |

The YMC-Pack ODS-AQ column used for the chromatography of the compounds is manufactured by YMC, Alte Raesfelderstrasse 6, 46514 Schermbeck, Germany.

TABLE A1
Compounds of the formula (I) in which $R_1$ is sec-butyl (B1a) or isopropyl (B1b)
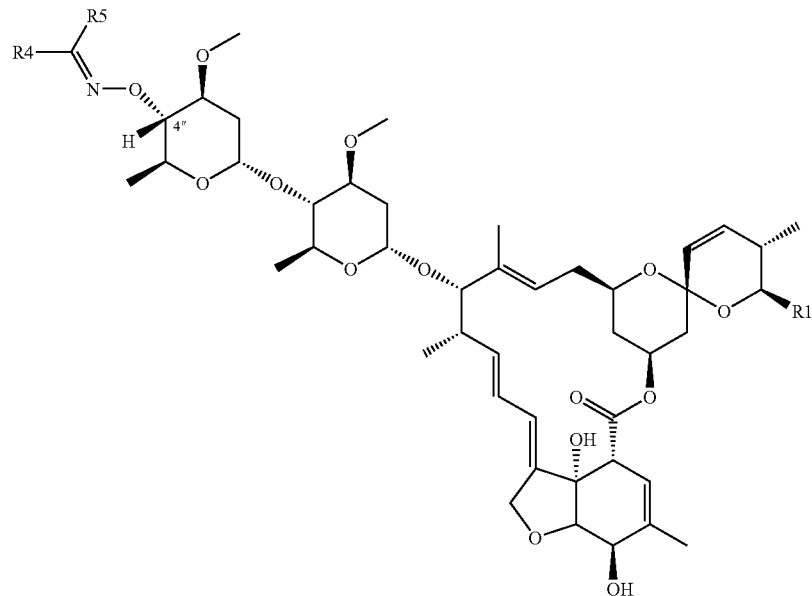
| No. | $R_4$ | $R_5$ | Retention time (min) B1a | B1b |
|---|---|---|---|---|
| A1.1 | Methyl | H | 11.09 | |
| A1.2 | HO~~~ | H | 8.96 | 8.21 |
| A1.3 | Ethyl | H | 11.18 | 10.51 |
| A1.4 | Cl~~~ | H | 10.98 | 10.34 |
| A1.5 | $CCl_3$ | H | 12.31 | |
| A1.6 | cyclopropyl | H | 11.00 | 10.35 |
| A1.7 | COOH | H | 5.19 | |
| A1.8 | Phenyl | H | 12.69 | |
| A1.9 | (4-pyridyl) | H | 9.16 | |
| A1.10 | (tetraol chain) | H | 6.57 | 5.97 |
| A1.11 | (disaccharide) | H | 5.28 | 4.84 |
| A1.12 | methyl | methyl | 11.63 | |
| A1.13 | —$(CH_2)_4$— | | 12.33 | 11.59 |
| A1.14 | HO~~~ | HO~~~ | 7.99 | |

TABLE A1-continued
Compounds of the formula (I) in which $R_1$ is sec-butyl (B1a) or isopropyl (B1b)
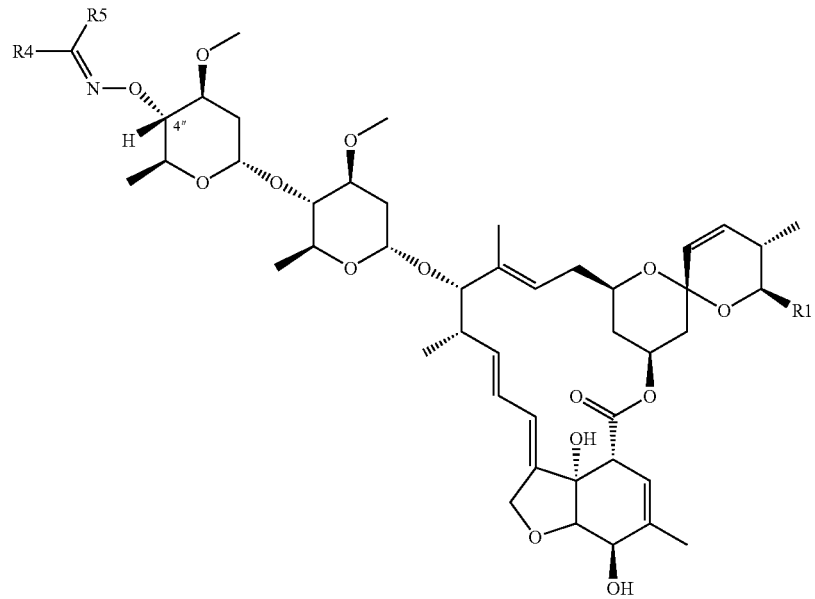
| No. | $R_4$ | $R_5$ | Retention time (min) B1a | B1b |
|---|---|---|---|---|
| A1.15 | H₂N—C(CH₃)₂— | methyl | 5.61 | 5.26 |
| A1.16 | HOCH₂—CH(OH)—CH(OH)—CH(OH)— | HO—CH₂— | 6.01 | |
| A1.17 | H | H | 11.27 | 10.57 |
| A1.18 | (CH₃)₂N—CH₂— | methyl | 5.17<br>5.04 | 4.75 |
| A1.19 | HO—CH₂— | methyl | 11.90 | 11.15 |
| A1.20 | CH₃—O—CH₂— | methyl | 13.35<br>13.21 | 12.93<br>12.79 |
| A1.21 | HO—CH₂—CH₂— | methyl | 11.96 | 11.21 |
| A1.22 | —(CH$_2$)$_2$—O—(CH$_2$)$_2$— | | 12.89 | 12.38 |
| A1.23 | —(CH$_2$)$_2$—N(CH$_3$)—(CH$_2$)$_2$— | | 5.16 | 4.72 |

TABLE A2
Compounds of the formula (I) in which $R_1$ is sec-butyl (B1a) or isopropyl (B1b).
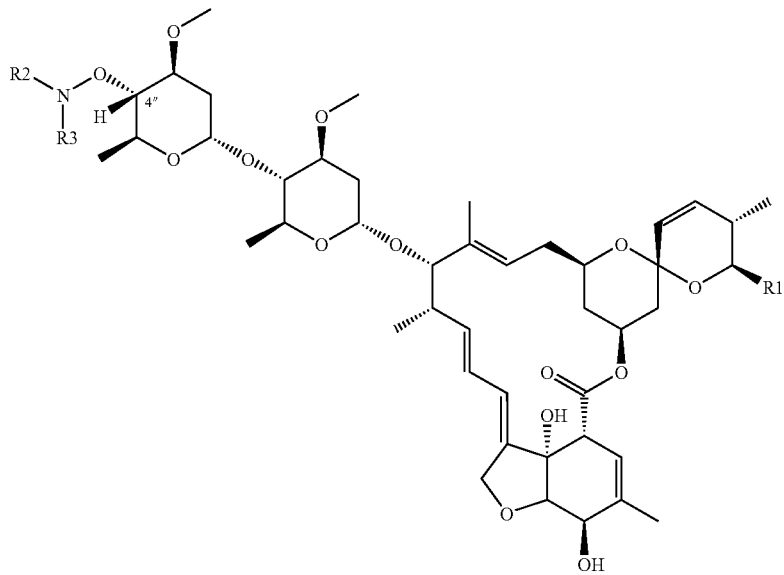
| No. | $R_2$ | $R_3$ | Retention time (min) B1a | Retention time (min) B1b |
|---|---|---|---|---|
| A2.1 | (phthaloyl, spans R2 and R3) | | | |
| A2.2 | H | H | 5.16 | 4.28 |
| A2.3 | acetyl | H | 7.90 | 7.22 |
| A2.4 | acryloyl | H | 8.28 | 7.63 |
| A2.5 | benzoyl | H | 9.31 | 8.56 |
| A2.7 | methoxyacetyl | H | 8.34 | 7.64 |
| A2.8 | isobutyryl | H | 8.86 | 8.14 |

TABLE A2-continued
Compounds of the formula (I) in which $R_1$ is sec-butyl (B1a) or isopropyl (B1b).
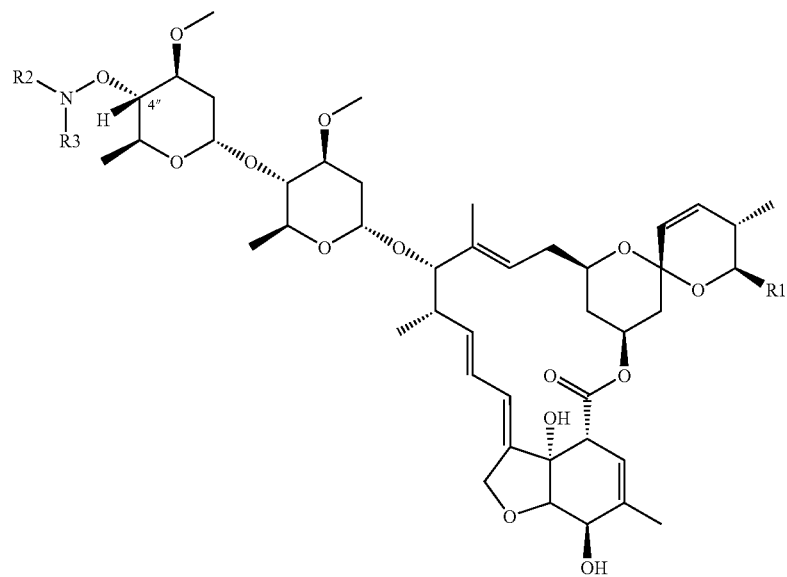
| No. | $R_2$ | $R_3$ | Retention time (min) B1a | B1b |
|---|---|---|---|---|
| A2.9 | (cyclopropyl-C(=O)-) | H | 8.70 | 8.00 |
| A2.10 | (ethyl-C(=O)-) | H | 8.45 | 7.75 |
| A2.11 | (MeO-C(=O)-) | H | 7.91 | 7.21 |
| A2.12 | (Me$_2$N-C(=O)-) | H | 8.09 | 7.41 |
| A2.13 | (H$_2$N-S(=O)$_2$-) | H | 7.80 | 7.15 |
| A2.14 | H | methyl | 8.00 | 7.31 |

TABLE A2-continued
Compounds of the formula (I) in which $R_1$ is sec-butyl (B1a) or isopropyl (B1b).
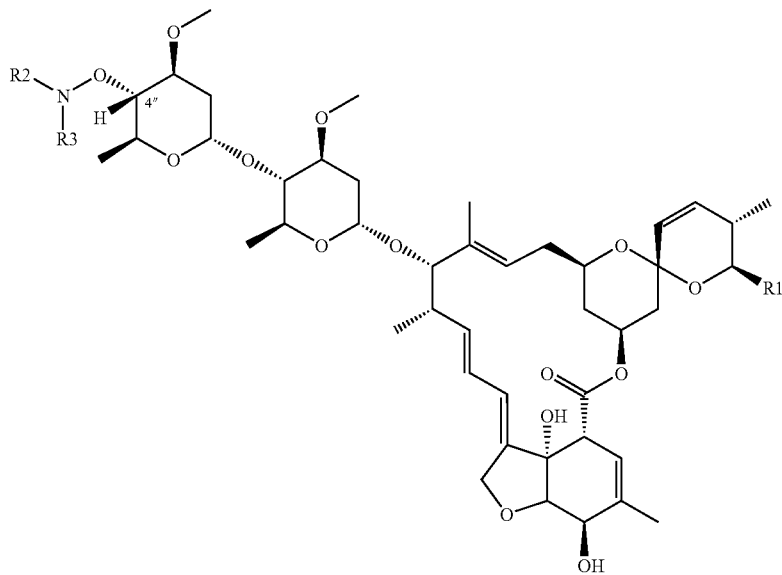
| No. | $R_2$ | $R_3$ | Retention time (min) B1a | Retention time (min) B1b |
|---|---|---|---|---|
| A2.15 | H₂N-C(=O)- | H | 8.16 | 8.96 |
| A2.16 | H-C(=O)- | methyl | | |
| A2.17 | CH₃-C(=O)- | methyl | | |
| A2.18 | CH₃O-CH₂-C(=O)- | methyl | | |
| A2.19 | methyl | methyl | 12.05 | 11.36 |

TABLE A3
Compounds of the formula (I) in which $R_1$ is sec-butyl (B1a) or isopropyl (B1b).
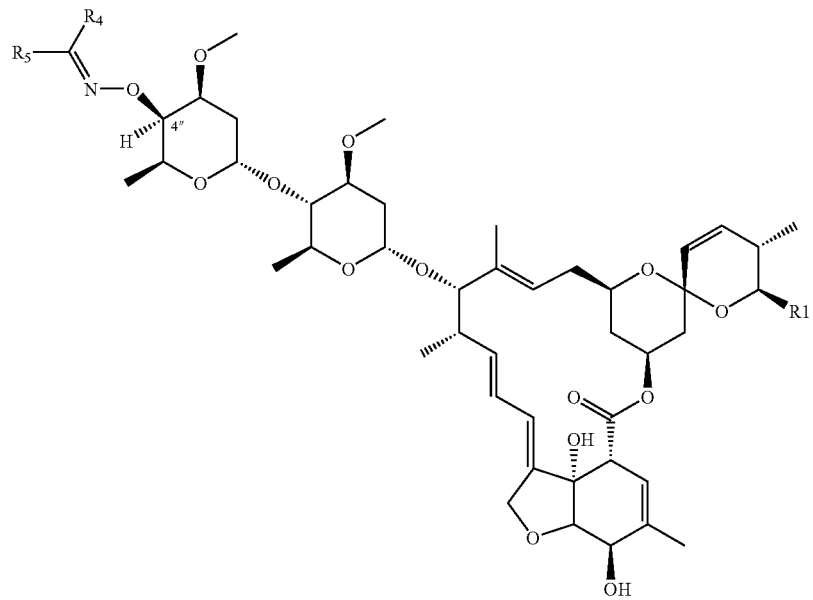
| No. | $R_4$ | $R_5$ | Retention time (min) B1a | B1b |
|---|---|---|---|---|
| A3.1 | Methyl | H | | |
| A3.2 | HO⟋⟋ | H | | |
| A3.3 | Ethyl | H | | |
| A3.4 | Cl⟋⟋ | H | | |
| A3.5 | CCl$_3$ | H | | |
| A3.6 | cyclopropyl | H | | |
| A3.7 | COOH | H | | |
| A3.8 | Phenyl | H | | |
| A3.9 | (4-pyridyl) | H | | |
| A3.10 | (polyol chain with 4 OH) | H | | |
| A3.11 | (glucosyl-polyol chain) | H | | |
| A3.12 | methyl | methyl | | |
| A3.13 | —(CH$_2$)$_4$— | | | |

TABLE A3-continued
Compounds of the formula (I) in which $R_1$ is sec-butyl (B1a) or isopropyl (B1b).
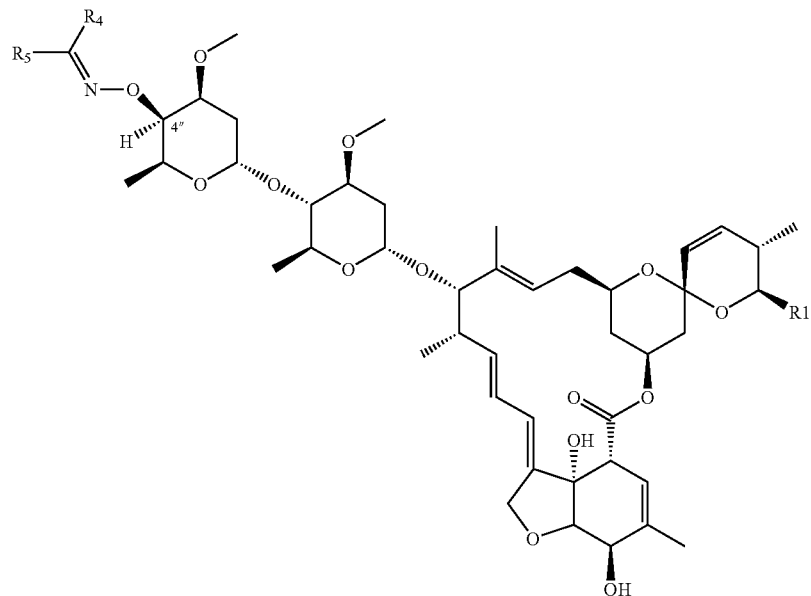
| No. | $R_4$ | $R_5$ | Retention time (min) B1a | B1b |
|---|---|---|---|---|
| A3.14 | HO⌇ | HO⌇ | | |
| A3.15 | H₂N-C(CH₃)₂⌇ | methyl | | |
| A3.16 | OH OH OH OH ⌇ | HO⌇ | | |

TABLE A4
Compounds of the formula (I) in which $R_1$ is sec-butyl or isopropyl
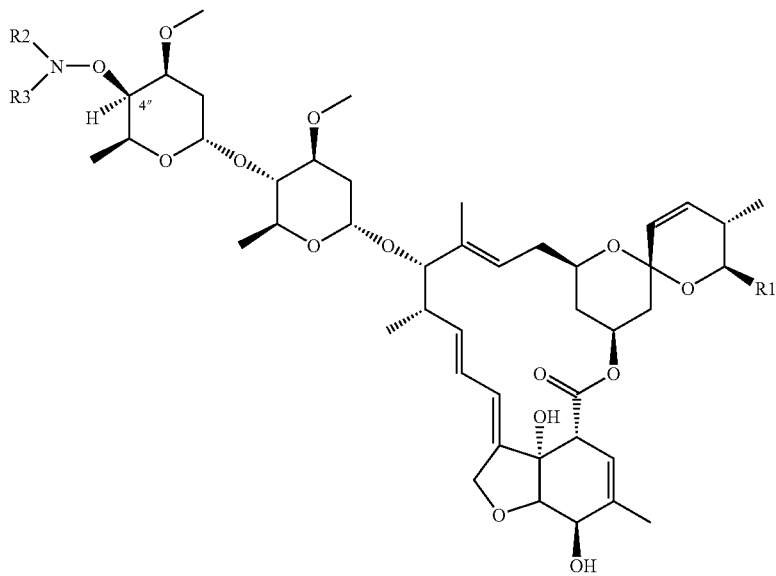
| No. | $R_2$ | $R_3$ | Retention time (min) B1a | B1b |
|---|---|---|---|---|
| A4.1 | \<phthaloyl group (benzene-1,2-dicarbonyl) spanning R2 and R3\> | | 9.98 | |
| A4.2 | H | H | 8.76 | 8.10 |

TABLE A5
Compounds of the formula (I) in which $R_1$ is sec-butyl (B1a) or isopropyl (B1b)
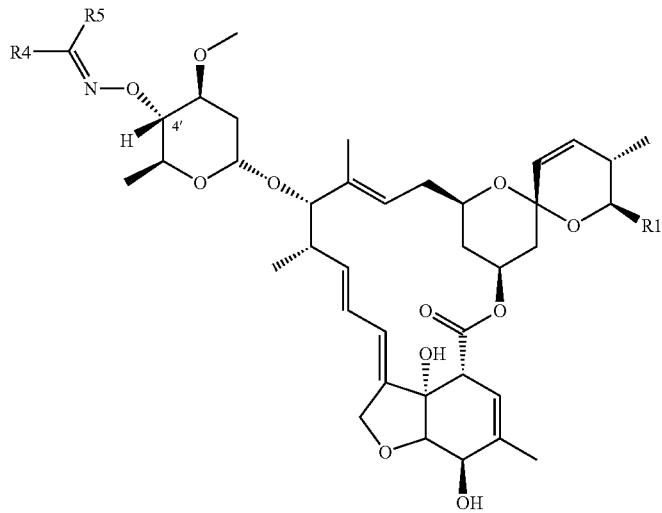
| No. | $R_4$ | $R_5$ | Retention time (min) B1a | B1b |
|---|---|---|---|---|
| A5.1 | Methyl | H | | |
| A5.2 | ∿ | H | 8.05 | |
| A5.3 | Ethyl | H | | |
| A5.4 | Cl∿ | H | | |
| A5.5 | cyclopropyl | H | | |
| A5.6 | COOH | H | 8.48 | |
| A5.7 | Phenyl | H | 12.12 | |
| A5.8 | pyridyl | H | | |
| A5.9 | methyl | methyl | 10.77 | |
| A5.10 | —(CH$_2$)$_4$— | | 11.41 | |
| A5.11 | ∿ | ∿ | 7.20 | |
| A5.12 | H$_2$N— | methyl | | |
| A5.13 | —(CH$_2$)$_2$—N(CH$_3$)—(CH$_2$)$_2$— | | 5.32 | |
| A5.14 | —(CH$_2$)$_2$—O—(CH$_2$)$_2$— | | 10.24 | |
| A5.15 | CH$_3$(CH$_2$)$_2$CH(CH$_3$)— | H | 13.01 | |
| A5.16 | (CH$_3$CH$_2$)$_2$CH— | H | 12.91 | |
| A5.17 | n-pentyl | H | 12.91 | |
| A5.18 | MeO—CH(OMe)— | H | 10.40 | |
| A5.19 | —(CH$_2$)$_3$— | | 10.88 | |
| A5.20 | —(CH$_2$)$_5$— | | 12.21 | |
| A5.21 | HO(CH$_2$)$_4$— | H | 9.13 | |

TABLE A5-continued
Compounds of the formula (I) in which $R_1$ is sec-butyl (B1a) or isopropyl (B1b)
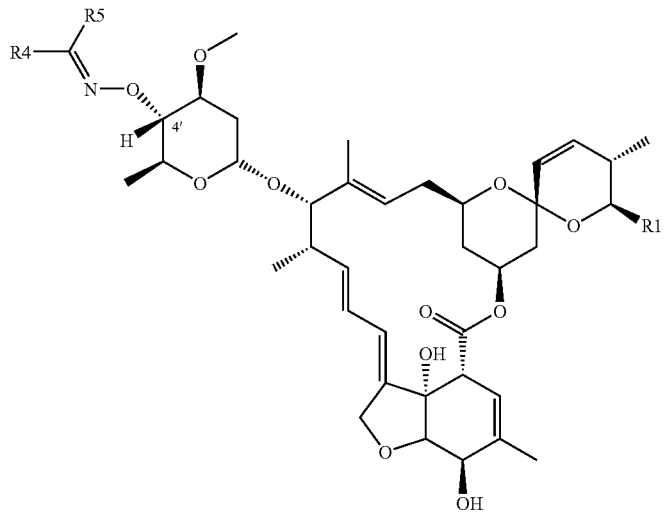
| No. | $R_4$ | $R_5$ | Retention time (min) B1a | B1b |
|---|---|---|---|---|
| A5.22 | (sec-butyl group) | methyl | 8.37 | |
| A5.23 | HO-CH2CH2- | methyl | 9.02 | |
| A5.24 | Me2N-CH2- | methyl | 5.28 | |
| A5.25 | MeO-CH2- | methyl | 10.88 | |
| A5.26 | MeS-CH2- | methyl | 11.84 | |
| A5.27 | Cl-CH(CH3)- | methyl | 12.01 | |
| A5.28 | F3C— | methyl | 11.79 | |
| A5.29 | ethyl | ethyl | 12.71 | |
| A5.30 | 4-Br-C6H4- | H | 12.98 | |
| A5.31 | 2,4-Cl2-C6H3- | H | 14.19 | |
| A5.32 | (N-methylpyrrolidinyl) | | 5.87 | |
| A5.33 | H | H | | |

TABLE A6
Compounds of the formula (I) in which $R_1$ is sec-butyl (B1a) or isopropyl (B1b).
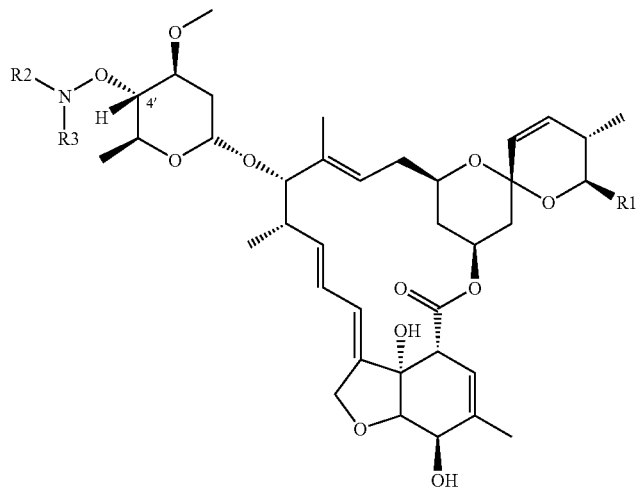
| No. | $R_2$ | $R_3$ | Retention time (min) B1a | B1b |
|---|---|---|---|---|
| A6.1 | (phthaloyl, both bonds to N) | | 11.50 | |
| A6.2 | H | H | 5.51 | |
| A6.3 | acetyl | H | 7.57 | |
| A6.4 | acryloyl | H | | |
| A6.5 | benzoyl | H | | |
| A6.6 | methoxyacetyl | H | 8.14 | |
| A6.7 | isobutyryl | H | 8.80 | |
| A6.8 | cyclopropanecarbonyl | H | | |

TABLE A6-continued
Compounds of the formula (I) in which $R_1$ is sec-butyl (B1a) or isopropyl (B1b).
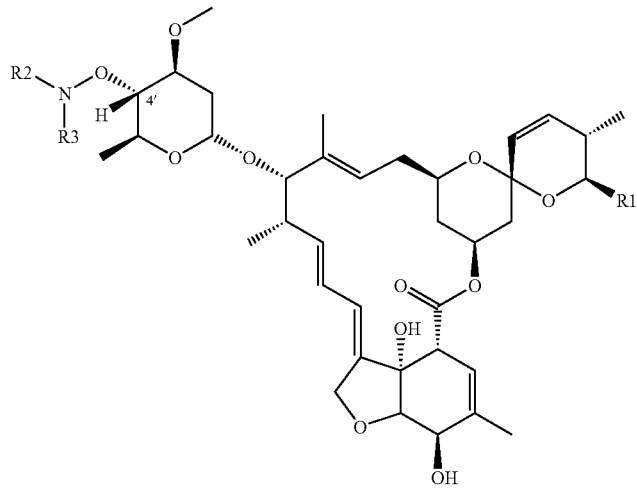
| No. | $R_2$ | $R_3$ | Retention time (min) | |
| --- | --- | --- | --- | --- |
| | | | B1a | B1b |
| A6.9 | ![propanoyl] | H | | |
| A6.10 | ![methoxycarbonyl] | H | | |
| A6.11 | ![dimethylaminocarbonyl] | H | | |
| A6.12 | ![sulfamoyl] | H | | |
| A6.13 | ![4-chlorobenzoyl] | H | | |
| A6.14 | ![crotonoyl] | H | 8.64 | |
| A6.15 | methyl | H | | |
| A6.16 | ![acetyl] | methyl | | |
| A6.17 | ![methoxyacetyl] | methyl | | |

TABLE A6-continued
Compounds of the formula (I) in which R₁ is sec-butyl (B1a) or isopropyl (B1b).
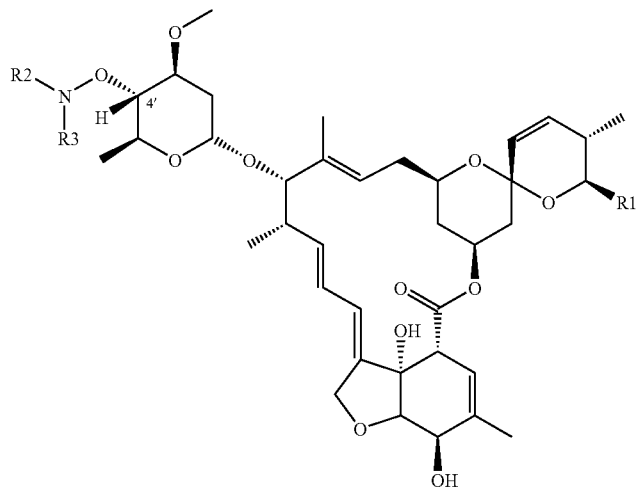
| No. | R₂ | R₃ | Retention time (min) B1a | B1b |
|---|---|---|---|---|
| A6.18 | <image of CHO group> | methyl | | |
TABLE A7
Compounds of the formula (I) in which R₁ is sec-butyl (B1a) or isopropyl (B1b).
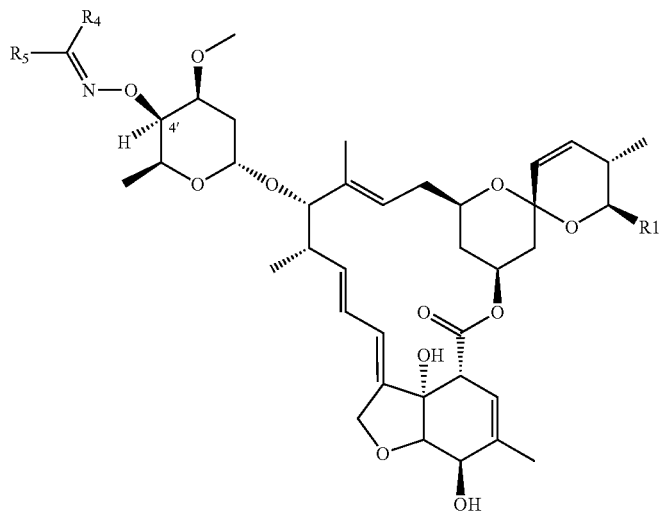
| No. | R₄ | R₅ | Retention time (min) B1a | B1b |
|---|---|---|---|---|
| A7.1 | Methyl | H | | |
| A7.2 | HO— | H | | |
| A7.3 | Ethyl | H | | |
| A7.4 | Cl— | H | | |

TABLE A7-continued
Compounds of the formula (I) in which $R_1$ is sec-butyl (B1a) or isopropyl (B1b).
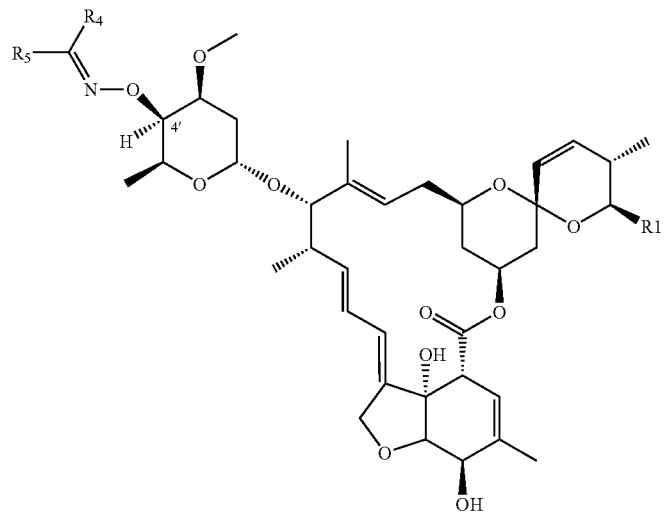
| | | | Retention time (min) | |
|---|---|---|---|---|
| No. | $R_4$ | $R_5$ | B1a | B1b |
| A7.5 | $CCl_3$ | H | | |
| A7.6 | cyclopropyl | H | | |
| A7.7 | COOH | H | | |
| A7.8 | Phenyl | H | | |
| A7.9 | methyl | methyl | | |
| A7.10 | —$(CH_2)_4$— | | | |

TABLE A8
Compounds of the formula (I) in which $R_1$ is sec-butyl (B1a) or isopropyl (B1b).
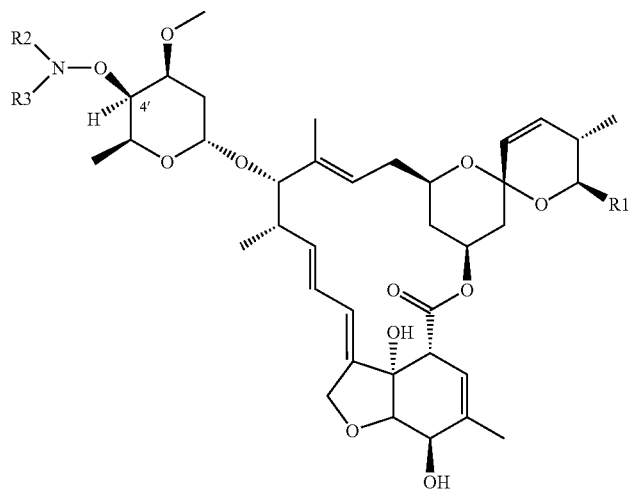
| | | | Retention time (min) | |
| --- | --- | --- | --- | --- |
| No. | $R_2$ | $R_3$ | B1a | B1b |
| A8.1 | 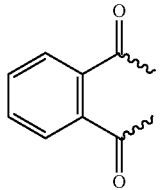 | | | |
| A8.2 | H | H | | |

TABLE B

Compounds of the formula

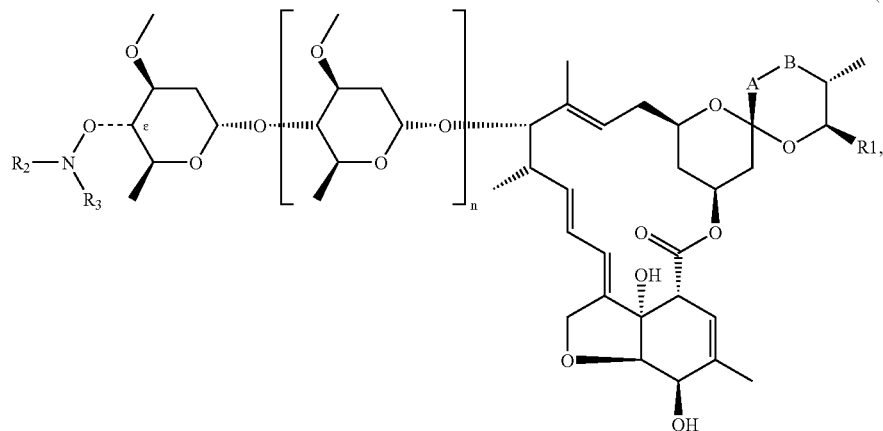

(IA)

and of the formula

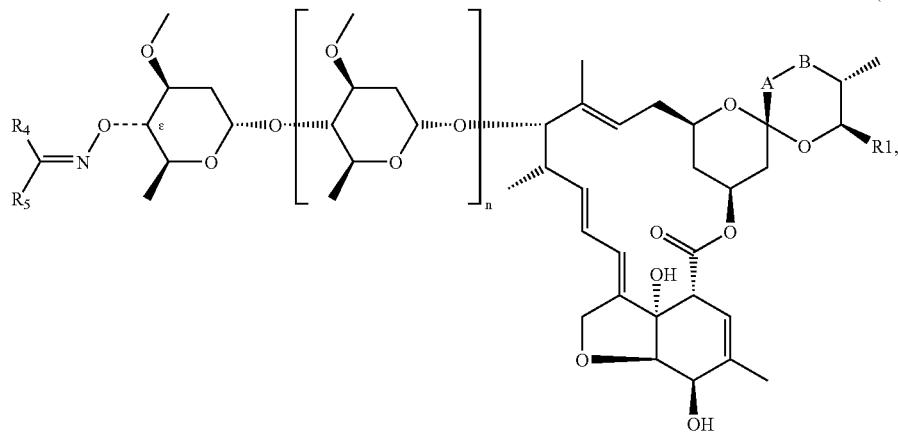

(IB)

wherein the combination of $R_2$ and $R_3$ holds for compound (IA)
and the combination of $R_4$ and $R_5$ holds for compound (IB):

| | $R_2$ or $R_4$ | $R_3$ or $R_5$ |
|---|---|---|
| B.1 | H | H |
| B.2 | Methyl | H |
| B.3 | Ethyl | H |
| B.4 | n-propyl | H |
| B.5 | iso-propyl | H |
| B.6 | n-butyl | H |
| B.7 | s-butyl | H |
| B.8 | iso-butyl | H |
| B.9 | t-butyl | H |
| B.10 | $CH_3(CH_2)_2CH(CH_3)-$ | H |
| B.11 | $(CH_3CH_2)_2CH-$ | H |
| B.12 | n-pentyl | H |
| B.13 | $CH_2=CH-CH_2-$ | H |
| B.14 | $CH_3-CH=CH-CH_2-$ | H |
| B.15 | $HO-CH_2-$ | H |
| B.16 | $HO-CH_2-CH_2-$ | H |
| B.17 | $CH_3-CH(OH)-$ | H |
| B.18 | $(CH_3)_2C(OH)-$ | H |
| B.19 | $HO-CH_2-CH_2-CH_2-$ | H |
| B.20 | $HO-CH_2-CH_2-CH_2-CH_2-$ | H |
| B.21 | $CH_3-O-CH_2-$ | H |
| B.22 | $CH_3-O-CH_2-CH_2-$ | H |
| B.23 | $CH_3-CH_2-O-CH_2-$ | H |
| B.24 | $CH_3-CH_2-O-CH_2-CH_2-$ | H |
| B.25 | $(CH_3O)_2CH-$ | H |
| B.26 | $NH_2-CH_2-$ | H |
| B.27 | $CF_3-$ | H |
| B.28 | $CH_2F$ | H |

TABLE B-continued

| | | |
|---|---|---|
| B.29 | CHF$_2$ | H |
| B.30 | CH$_2$Cl | H |
| B.31 | CHCl$_2$ | H |
| B.32 | CCl$_3$ | H |
| B.33 | CN | H |
| B.34 | Phenyl | H |
| B.35 | Benzyl | H |
| B.36 | phenethyl | H |
| B.37 | 2-methylphenyl | H |
| B.38 | 3-methylphenyl | H |
| B.39 | 4-methylphenyl | H |
| B.40 | 4-fluorophenyl | H |
| B.41 | 4-chlorophenyl | H |
| B.42 | 2,4-dichlorophenyl | H |
| B.43 | 4-bromophenyl | H |
| B.44 | 4-methoxyphenyl | H |
| B.45 | benzo[1,3]dioxol-5-yl | H |
| B.46 | 2,2-difluorobenzo[1,3]dioxol-5-yl | H |
| B.47 | pyrid-2-yl | H |
| B.48 | pyrid-3-yl | H |

TABLE B-continued
| B.49 | pyrid-4-yl | H |
| B.50 | 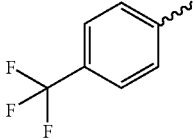 | H |
| B.51 | 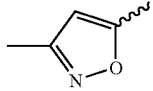 | H |
| B.52 | 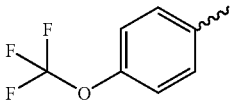 | H |
| B.53 | 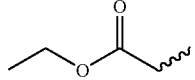 | H |
| B.54 | 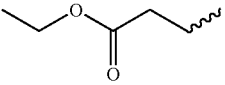 | H |
| B.55 |  | H |
| B.56 |  | H |
| B.57 | 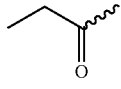 | H |
| B.58 | 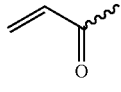 | H |
| B.59 | 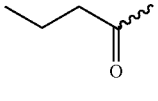 | H |
| B.60 | 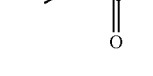 | H |
| B.61 | 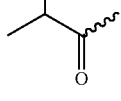 | H |
| B.62 | 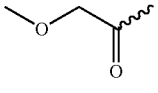 | H |
| B.63 | 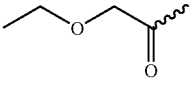 | H |

TABLE B-continued

| | | |
|---|---|---|
| B.64 | HOCH₂CH₂-O-CH₂-C(=O)- | H |
| B.65 | benzoyl | H |
| B.66 | methoxycarbonyl (MeO-C(=O)-) | H |
| B.67 | ethoxycarbonyl (EtO-C(=O)-) | H |
| B.68 | H₂N-C(=O)- | H |
| B.69 | MeNH-C(=O)- | H |
| B.70 | Me₂N-C(=O)- | H |
| B.71 | PhNH-C(=O)- | H |
| B.72 | SO₂Me | H |
| B.73 | SO₂Et | H |
| B.74 | ethyl | methyl |
| B.75 | CH₂OH | methyl |
| B.76 | 2-hydroxyethyl | methyl |
| B.77 | methoxymethyl | methyl |
| B.78 | methylthiomethyl | methyl |
| B.79 | CF₃ | methyl |
| B.80 | CH₃—CHCl— | methyl |
| B.81 | CH₂=CH—CH₂— | methyl |
| B.82 | phenyl | methyl |
| B.83 | benzyl | methyl |
| B.84 | EtO-C(=O)-CH₂- | methyl |
| B.85 | H-C(=O)- (formyl) | methyl |
| B.86 | acetyl | methyl |
| B.87 | acryloyl (CH₂=CH-C(=O)-) | methyl |

TABLE B-continued

| | | |
|---|---|---|
| B.88 | (isobutyryl group: (CH3)2CH-C(=O)-) | methyl |
| B.89 | (methoxyacetyl group: CH3-O-CH2-C(=O)-) | methyl |
| B.90 | (benzoyl group: Ph-C(=O)-) | methyl |
| B.91 | (methoxycarbonyl group: CH3-O-C(=O)-) | methyl |
| B.92 | (dimethylamino group: (CH3)2N-) | methyl |
| B.93 | (dimethylcarbamoyl group: (CH3)2N-C(=O)-) | methyl |
| B.94 | (phenylcarbamoyl group: Ph-NH-C(=O)-) | methyl |
| B.95 | H | ethyl |
| B.96 | H | n-propyl |
| B.97 | H | iso-propyl |
| B.98 | H | n-butyl |
| B.99 | H | s-butyl |
| B.100 | H | iso-butyl |
| B.101 | H | t-butyl |
| B.102 | H | $CH_3(CH_2)_2CH(CH_3)-$ |
| B.103 | H | $(CH_3CH_2)_2CH-$ |
| B.104 | H | n-pentyl |
| B.105 | H | $CH_2=CH-CH_2-$ |
| B.106 | H | $CH_3-CH=CH-CH_2-$ |
| B.107 | H | $HO-CH_2-$ |
| B.108 | H | $HO-CH_2-CH_2-$ |
| B.109 | H | $CH_3-CH(OH)-$ |
| B.110 | H | $(CH_3)_2C(OH)-$ |
| B.111 | H | $HO-CH_2-CH_2-CH_2-$ |
| B.112 | H | $HO-CH_2-CH_2-CH_2-CH_2-$ |
| B.113 | H | $CH_3-O-CH_2-$ |
| B.114 | H | $CH_3-O-CH_2-CH_2-$ |
| B.115 | H | $CH_3-CH_2-O-CH_2-$ |
| B.116 | H | $CH_3-CH_2-O-CH_2-CH_2-$ |
| B.117 | H | $(CH_3O)_2CH-$ |
| B.118 | H | $NH_2-CH_2-$ |
| B.119 | H | $CF_3-$ |
| B.120 | H | $CH_2F$ |
| B.121 | H | $CHF_2$ |
| B.122 | H | $CH_2Cl$ |
| B.123 | H | $CHCl_2$ |
| B.124 | H | $CCl_3$ |
| B.125 | H | CN |
| B.126 | H | phenyl |
| B.127 | H | Benzyl |

TABLE B-continued
| | | |
|---|---|---|
| B.128 | H | 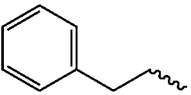 |
| B.129 | H | 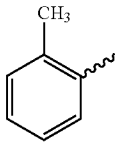 |
| B.130 | H | 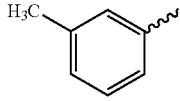 |
| B.131 | H | 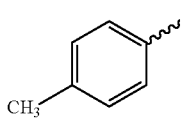 |
| B.132 | H | 4-F-phenyl |
| B.133 | H | 4-Cl-phenyl |
| B.134 | H | 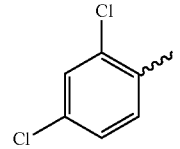 |
| B.135 | H | 4-Br-phenyl |
| B.136 | H | 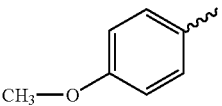 |
| B.137 | H | 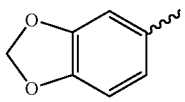 |
| B.138 | H | 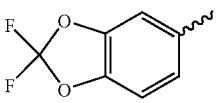 |
| B.139 | H | pyrid-2-yl |
| B.140 | H | pyrid-3-yl |
| B.141 | H | pyrid-4-yl |
| B.142 | H | 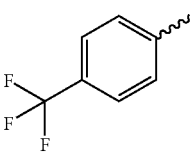 |
| B.143 | H | 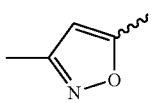 |
| B.144 | H | 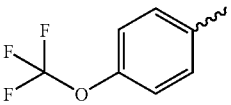 |

TABLE B-continued
| B.145 | H | 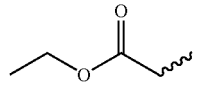 |
| B.146 | H | 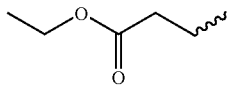 |
| B.147 | H |  |
| B.148 | H |  |
| B.149 | H | 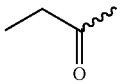 |
| B.150 | H | 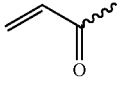 |
| B.151 | H | 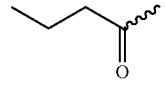 |
| B.152 | H | 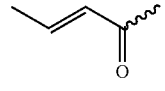 |
| B.153 | H | 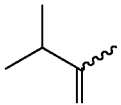 |
| B.154 | H | 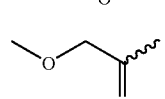 |
| B.155 | H | 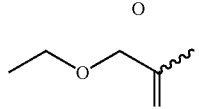 |
| B.156 | H | 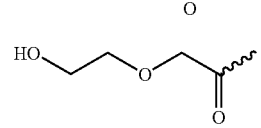 |
| B.157 | H | benzoyl |
| B.158 | H | 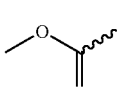 |
| B.159 | H | 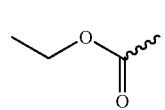 |
| B.160 | H |  |

TABLE B-continued
| B.161 | H | 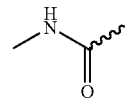 |
| B.162 | H | 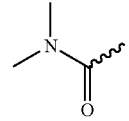 |
| B.163 | H | 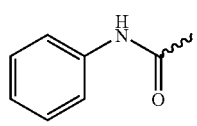 |
| B.164 | H | SO$_2$Me |
| B.165 | H | SO$_2$Et |
| B.166 | methyl | ethyl |
| B.167 | methyl | CH$_2$=CH—CH$_2$— |
| B.168 | methyl | phenyl |
| B.169 | methyl | hydroxymethyl |
| B.170 | methyl | 2-hydroxyethyl |
| B.171 | methyl | methoxymethyl |
| B.172 | methyl | methylthiomethyl |
| B.173 | methyl | CF$_3$ |
| B.174 | methyl | CH$_3$—CHCl— |
| B.175 | methyl | benzyl |
| B.176 | methyl | 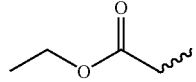 |
| B.177 | methyl |  |
| B.178 | methyl |  |
| B.179 | methyl | 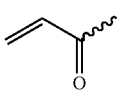 |
| B.180 | methyl | 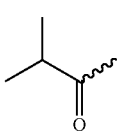 |
| B.181 | methyl | 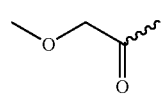 |
| B.182 | methyl | benzoyl |
| B.183 | methyl | 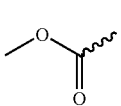 |
| B.184 | methyl | 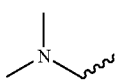 |

TABLE B-continued
| | | |
|---|---|---|
| B.185 | methyl | 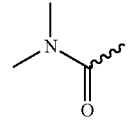 |
| B.186 | methyl | 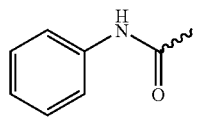 |
| B.187 | methyl | —CN |
| B.188 | methyl | methyl |
| B.189 | ethyl | ethyl |
| B.190 | hydroxymethyl | ethyl |
| B.191 | hydroxymethyl | $CH_2=CH—CH_2—$ |
| B.192 | hydroxymethyl | 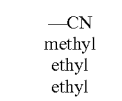 |
| B.193 | hydroxymethyl | 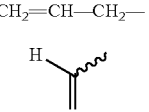 |
| B.194 | hydroxymethyl | 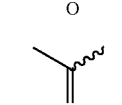 |
| B.195 | hydroxymethyl | 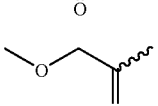 |
| B.196 | hydroxymethyl | —CN |
| B.197 | $—CH_2—CH=CH_2$ | ethyl |
| B.198 | 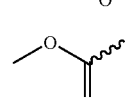 | ethyl |
| B.199 | 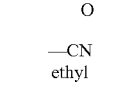 | ethyl |
| B.200 | 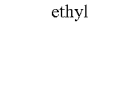 | ethyl |
| B.201 |  | ethyl |
| B.202 | $CH_2=CH—CH_2—$ | $CH_2=CH—CH_2—$ |
| B.203 | $CH_2=CH—CH_2—$ | 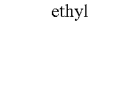 |
| B.204 | $CH_2=CH—CH_2—$ | 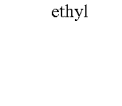 |
| B.205 | $CH_2=CH—CH_2—$ | 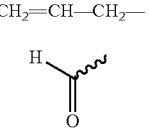 |

TABLE B-continued
| | | |
|---|---|---|
| B.206 | CH₂=CH—CH₂— | 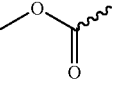 |
| B.207 | CH₂=CH—CH₂— | —CN |
| B.208 |  | CH₂=CH—CH₂— |
| B.209 |  | CH₂=CH—CH₂— |
| B.210 | 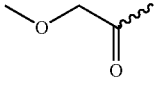 | CH₂=CH—CH₂— |
| B.211 | 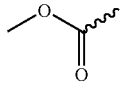 | CH₂=CH—CH₂— |
| B.212 | —CH₂—CH₂—CH₂— | |
| B.213 | —CH₂—CH=CH— | |
| B.214 | 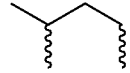 | |
| B.215 | 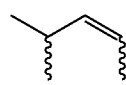 | |
| B.216 | 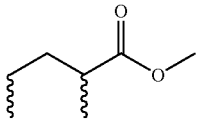 | |
| B.217 | 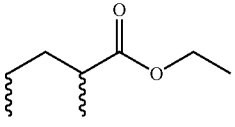 | |
| B.218 | 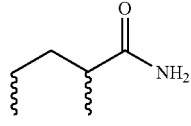 | |
| B.219 | 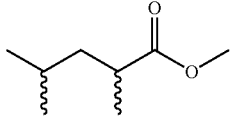 | |
| B.220 | 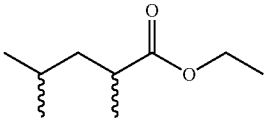 | |
| B.221 | 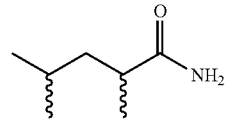 | |

TABLE B-continued
| | |
|---|---|
| B.222 | 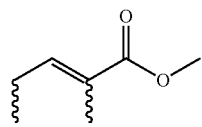 |
| B.223 | 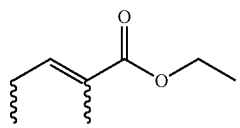 |
| B.224 | 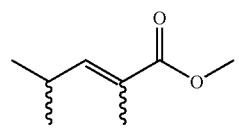 |
| B.225 | 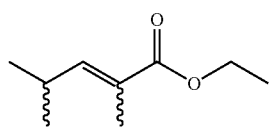 |
| B.226 | 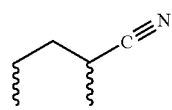 |
| B.227 | 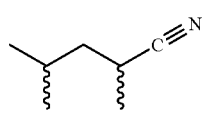 |
| B.228 | 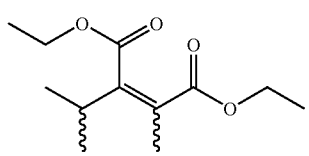 |
| B.229 | 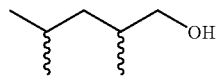 |
| B.230 | 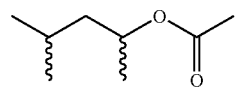 |
| B.231 | 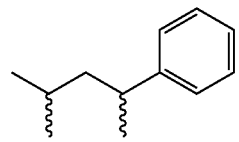 |
| B.232 | 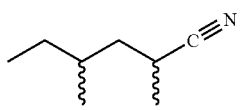 |
| B.233 | 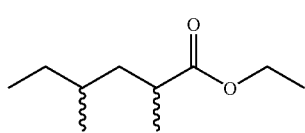 |

TABLE B-continued
| B.234 | 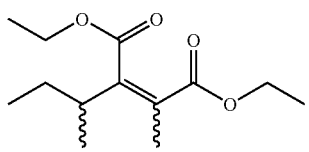 |
| B.235 | 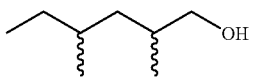 |
| B.236 | 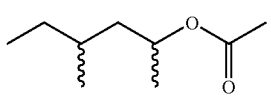 |
| B.237 | 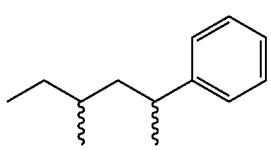 |
| B.238 | 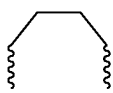 |
| B.239 | 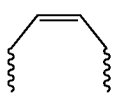 |
| B.240 |  |
| B.241 | 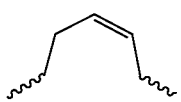 |
| B.242 | 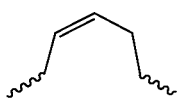 |
| B.243 | 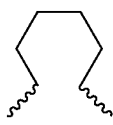 |
| B.244 | 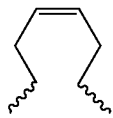 |
| B.245 | 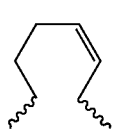 |
| B.246 | 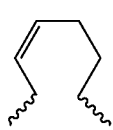 |

TABLE B-continued

B.247
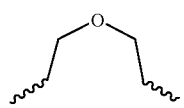

B.248
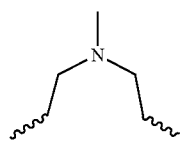

B.249
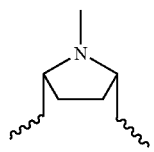

Table 1: A compound of the formula (IA) in which the configuration at the ε-position is S, n is 1, A-B is —CH═CH—, $R_1$ is sec-butyl or isopropyl and the combination of $R_2$ and $R_3$ for each compounds corresponds to a line B.1 to B.249 of Table B.

Table 2: A compound of the formula (IA) in which the configuration at the ε-position is S, n is 1, A-B is —CH$_2$—CH$_2$—, $R_1$ is sec-butyl or isopropyl and the combination of $R_2$ and $R_3$ for each compounds corresponds to a line B.1 to B.249 of Table B.

Table 3: A compound of the formula (IA) in which the configuration at the ε-position is S, n is 0, A-B is —CH═CH—, $R_1$ is sec-butyl or isopropyl and the combination of $R_2$ and $R_3$ for each compounds corresponds to a line B.1 to B.249 of Table B.

Table 4: A compound of the formula (IA) in which the configuration at the ε-position is S, n is 0, A-B is —CH$_2$—CH$_2$—, $R_1$ is sec-butyl or isopropyl and the combination of $R_2$ and $R_3$ for each compounds corresponds to a line B.1 to B.249 of Table B.

Table 5: A compound of the formula (IA) in which the configuration at the ε-position is R, n is 1, A-B is —CH═CH—, $R_1$ is sec-butyl or isopropyl and the combination of $R_2$ and $R_3$ for each compounds corresponds to a line B.1 to B.249 of Table B.

Table 6: A compound of the formula (IA) in which the configuration at the ε-position is R, n is 1, A-B is —CH$_2$—CH$_2$—, $R_1$ is sec-butyl or isopropyl and the combination of $R_2$ and $R_3$ for each compounds corresponds to a line B.1 to B.249 of Table B.

Table 7: A compound of the formula (IA) in which the configuration at the ε-position is R, n is 0, A-B is —CH═CH—, $R_1$ is sec-butyl or isopropyl and the combination of $R_2$ and $R_3$ for each compounds corresponds to a line B.1 to B.249 of Table B.

Table 8: A compound of the formula (IA) in which the configuration at the ε-position is R, n is 0, A-B is —CH$_2$—CH$_2$—, $R_1$ is sec-butyl or isopropyl and the combination of $R_2$ and $R_3$ for each compounds corresponds to a line B.1 to B.249 of Table B.

Table 9: A compound of the formula (IB) in which the configuration at the ε-position is S, n is 1, A-B is —CH═CH—, $R_1$ is sec-butyl or isopropyl and the combination of $R_4$ and $R_5$ for each compounds corresponds to a line B.1 to B.249 of Table B.

Table 10: A compound of the formula (IB) in which the configuration at the ε-position is S, n is 1, A-B is —CH$_2$—CH$_2$—, $R_1$ is sec-butyl or isopropyl and the combination of $R_4$ and $R_5$ for each compounds corresponds to a line B.1 to B.249 of Table B.

Table 11: A compound of the formula (IB) in which the configuration at the ε-position is S, n is 0, A-B is —CH═CH—, $R_1$ is sec-butyl or isopropyl and the combination of $R_4$ and $R_5$ for each compounds corresponds to a line B.1 to B.249 of Table B.

Table 12: A compound of the formula (IB) in which the configuration at the ε-position is S, n is 0, A-B is —CH$_2$—CH$_2$—, $R_1$ is sec-butyl or isopropyl and the combination of $R_4$ and $R_5$ for each compounds corresponds to a line B.1 to B.249 of Table B.

Table 13: A compound of the formula (IB) in which the configuration at the ε-position is R, n is 1, A-B is —CH═CH—, $R_1$ is sec-butyl or isopropyl and the combination of $R_4$ and $R_5$ for each compounds corresponds to a line B.1 to B.249 of Table B.

Table 14: A compound of the formula (IB) in which the configuration at the ε-position is R, n is 1, A-B is —CH$_2$—CH$_2$—, $R_1$ is sec-butyl or isopropyl and the combination of $R_4$ and $R_5$ for each compounds corresponds to a line B.1 to B.249 of Table B.

Table 15: A compound of the formula (IB) in which the configuration at the ε-position is R, n is 0, A-B is —CH═CH—, $R_1$ is sec-butyl or isopropyl and the combination of $R_4$ and $R_5$ for each compounds corresponds to a line B.1 to B.249 of Table B.

Table 16: A compound of the formula (IB) in which the configuration at the ε-position is R, n is 0, A-B is —CH$_2$—CH$_2$—, $R_1$ is sec-butyl or isopropyl and the combination of $R_4$ and $R_5$ for each compounds corresponds to a line B.1 to B.249 of Table B.

Table 17: A compound of the formula (IA) in which the configuration at the ε-position is S, n is 1, A-B is —CH═CH—, $R_1$ is cyclohexyl and the combination of $R_2$ and $R_3$ for each compounds corresponds to a line B.1 to B.249 of Table B.

Table 18: A compound of the formula (IA) in which the configuration at the ε-position is S, n is 1, A-B is —CH$_2$—CH$_2$—, $R_1$ is cyclohexyl and the combination of $R_2$ and $R_3$ for each compounds corresponds to a line B.1 to B.249 of Table B.

Table 19: A compound of the formula (IA) in which the configuration at the ε-position is S, n is 0, A-B is —CH=CH—, $R_1$ is cyclohexyl and the combination of $R_2$ and $R_3$ for each compounds corresponds to a line B.1 to B.249 of Table B.

Table 20: A compound of the formula (IA) in which the configuration at the ε-position is S, n is 0, A-B is —CH$_2$—CH$_2$—, $R_1$ is cyclohexyl and the combination of $R_2$ and $R_3$ for each compounds corresponds to a line B.1 to B.249 of Table B.

Table 21: A compound of the formula (IA) in which the configuration at the ε-position is R, n is 1, A-B is —CH=CH—, $R_1$ is cyclohexyl and the combination of $R_2$ and $R_3$ for each compounds corresponds to a line B.1 to B.249 of Table B.

Table 22: A compound of the formula (IA) in which the configuration at the ε-position is R, n is 1, A-B is —CH$_2$—CH$_2$—, $R_1$ is cyclohexyl and the combination of $R_2$ and $R_3$ for each compounds corresponds to a line B.1 to B.249 of Table B.

Table 23: A compound of the formula (IA) in which the configuration at the ε-position is R, n is 0, A-B is —CH=CH—, $R_1$ is cyclohexyl and the combination of $R_2$ and $R_3$ for each compounds corresponds to a line B.1 to B.249 of Table B.

Table 24: A compound of the formula (IA) in which the configuration at the ε-position is R, n is 0, A-B is —CH$_2$—CH$_2$—, $R_1$ is cyclohexyl and the combination of $R_2$ and $R_3$ for each compounds corresponds to a line B.1 to B.249 of Table B.

Table 25: A compound of the formula (IB) in which the configuration at the ε-position is S, n is 1, A-B is —CH=CH—, $R_1$ is cyclohexyl and the combination of $R_4$ and $R_5$ for each compounds corresponds to a line B.1 to B.249 of Table B.

Table 26: A compound of the formula (IB) in which the configuration at the ε-position is S, n is 1, A-B is —CH$_2$—CH$_2$—, $R_1$ is cyclohexyl and the combination of $R_4$ and $R_5$ for each compounds corresponds to a line B.1 to B.249 of Table B.

Table 27: A compound of the formula (IB) in which the configuration at the ε-position is S, n is 0, A-B is —CH=CH—, $R_1$ is cyclohexyl and the combination of $R_4$ and $R_5$ for each compounds corresponds to a line B.1 to B.249 of Table B.

Table 28: A compound of the formula (IB) in which the configuration at the ε-position is S, n is 0, A-B is —CH$_2$—CH$_2$—, $R_1$ is cyclohexyl and the combination of $R_4$ and $R_5$ for each compounds corresponds to a line B.1 to B.249 of Table B.

Table 29: A compound of the formula (IB) in which the configuration at the ε-position is R, n is 1, A-B is —CH=CH—, $R_1$ is cyclohexyl and the combination of $R_4$ and $R_5$ for each compounds corresponds to a line B.1 to B.249 of Table B.

Table 30: A compound of the formula (IB) in which the configuration at the ε-position is R, n is 1, A-B is —CH$_2$—CH$_2$—, $R_1$ is cyclohexyl and the combination of $R_4$ and $R_5$ for each compounds corresponds to a line B.1 to B.249 of Table B.

Table 31: A compound of the formula (IB) in which the configuration at the ε-position is R, n is 0, A-B is —CH=CH—, $R_1$ is cyclohexyl and the combination of $R_4$ and $R_5$ for each compounds corresponds to a line B.1 to B.249 of Table B.

Table 32: A compound of the formula (IB) in which the configuration at the ε-position is R, n is 0, A-B is —CH$_2$—CH$_2$—, $R_1$ is cyclohexyl and the combination of $R_4$ and $R_5$ for each compounds corresponds to a line B.1 to B.249 of Table B.

Table 33: A compound of the formula (IA) in which the configuration at the ε-position is S, n is 1, A-B is —CH=CH—, $R_1$ is 1-methyl-butyl and the combination of $R_2$ and $R_3$ for each compounds corresponds to a line B.1 to B.249 of Table B.

Table 34: A compound of the formula (IA) in which the configuration at the ε-position is S, n is 1, A-B is —CH$_2$—CH$_2$—, $R_1$ is 1-methyl-butyl and the combination of $R_2$ and $R_3$ for each compounds corresponds to a line B.1 to B.249 of Table B.

Table 35: A compound of the formula (IA) in which the configuration at the ε-position is S, n is 0, A-B is —CH=CH—, $R_1$ is 1-methyl-butyl and the combination of $R_2$ and $R_3$ for each compounds corresponds to a line B.1 to B.249 of Table B.

Table 36: A compound of the formula (IA) in which the configuration at the ε-position is S, n is 0, A-B is —CH$_2$—CH$_2$—, $R_1$ is 1-methyl-butyl and the combination of $R_2$ and $R_3$ for each compounds corresponds to a line B.1 to B.249 of Table B.

Table 37: A compound of the formula (IA) in which the configuration at the ε-position is R, n is 1, A-B is —CH=CH—, $R_1$ is 1-methyl-butyl and the combination of $R_2$ and $R_3$ for each compounds corresponds to a line B.1 to B.249 of Table B.

Table 38: A compound of the formula (IA) in which the configuration at the ε-position is R, n is 1, A-B is —CH$_2$—CH$_2$—, $R_1$ is 1-methyl-butyl and the combination of $R_2$ and $R_3$ for each compounds corresponds to a line B.1 to B.249 of Table B.

Table 39: A compound of the formula (IA) in which the configuration at the ε-position is R, n is 0, A-B is —CH=CH—, $R_1$ is 1-methyl-butyl and the combination of $R_2$ and $R_3$ for each compounds corresponds to a line B.1 to B.249 of Table B.

Table 40: A compound of the formula (IA) in which the configuration at the ε-position is R, n is 0, A-B is —CH$_2$—CH$_2$—, $R_1$ is 1-methyl-butyl and the combination of $R_2$ and $R_3$ for each compounds corresponds to a line B.1 to B.249 of Table B.

Table 41: A compound of the formula (IB) in which the configuration at the ε-position is S, n is 1, A-B is —CH=CH—, $R_1$ is 1-methyl-butyl and the combination of $R_4$ and $R_5$ for each compounds corresponds to a line B.1 to B.249 of Table B.

Table 42: A compound of the formula (IB) in which the configuration at the ε-position is S, n is 1, A-B is —CH$_2$—CH$_2$—, $R_1$ is 1-methyl-butyl and the combination of $R_4$ and $R_5$ for each compounds corresponds to a line B.1 to B.249 of Table B.

Table 43: A compound of the formula (IB) in which the configuration at the ε-position is S, n is 0, A-B is —CH=CH—, $R_1$ is 1-methyl-butyl and the combination of $R_4$ and $R_5$ for each compounds corresponds to a line B.1 to B.249 of Table B.

Table 44: A compound of the formula (IB) in which the configuration at the ε-position is S, n is 0, A-B is —CH$_2$—CH$_2$—, $R_1$ is 1-methyl-butyl and the combination of $R_4$ and $R_5$ for each compounds corresponds to a line B.1 to B.249 of Table B.

Table 45: A compound of the formula (IB) in which the configuration at the ε-position is R, n is 1, A-B is —CH=CH—, $R_1$ is 1-methyl-butyl and the combination of $R_4$ and $R_5$ for each compounds corresponds to a line B.1 to B.249 of Table B.

Table 46: A compound of the formula (IB) in which the configuration at the $\epsilon$-position is R, n is 1, A-B is —$CH_2$—$CH_2$—, $R_1$ is 1-methyl-butyl and the combination of $R_4$ and $R_5$ for each compounds corresponds to a line B.1 to B.249 of Table B.

Table 47: A compound of the formula (IB) in which the configuration at the $\epsilon$-position is R, n is 0, A-B is —CH=CH—, $R_1$ is 1-methyl-butyl and the combination of $R_4$ and $R_5$ for each compounds corresponds to a line B.1 to B.249 of Table B.

Table 48: A compound of the formula (IB) in which the configuration at the $\epsilon$-position is R, n is 0, A-B is —$CH_2$—$CH_2$—, $R_1$ is 1-methyl-butyl and the combination of $R_4$ and $R_5$ for each compounds corresponds to a line B.1 to B.249 of Table B.

Formulation examples for use in crop protection (%=percent by weight)

EXAMPLE F1

Emulsion concentrates

|  | a) | b) | c) |
|---|---|---|---|
| Active compound | 25% | 40% | 50% |
| Calcium dodecylbenzenesulphonate | 5% | 8% | 6% |
| Castor oil polyethylene glycol ether (36 mol of EO) | 5% | — | — |
| Tributylphenol polyethylene glycol ether (30 mol of EO) | — | 12% | 4% |
| Cyclohexanone | — | 15% | 20% |
| Xylene mixture | 65% | 25% | 20% |

Mixing of finely ground active compound and additives gives an emulsion concentrate which, by dilution with water, affords emulsions of the desired concentration.

EXAMPLE F2

Solutions

|  | a) | b) | c) | d) |
|---|---|---|---|---|
| active ingredient | 80% | 10% | 5% | 95% |
| ethylene glycol monomethyl ether | — | 20% | — | — |
| polyethylene glycol (MW 400) | — | 70% | — | — |
| N-methylpyrrolid-2-one | 20% | — | — | — |
| epoxidised coconut oil | — | — | 1% | 5% |
| petroleum ether (boiling range: 160-190° C.) | — | — | 94% | — |

Mixing of finely ground active compound and additives gives a solution suitable for use in the form of microdrops.

EXAMPLE F3

Granules

|  | a) | b) | c) | d) |
|---|---|---|---|---|
| Active compound | 5% | 10% | 8% | 21% |
| Kaolin | 94% | — | 79% | 54% |
| Finely divided silicic acid | 1% | — | 13% | 7% |
| Attapulgite | — | 90% | — | 18% |

The active compound is dissolved in dichloromethane, the solution is sprayed onto the mixture of carriers and the solvent is evaporated under reduced pressure.

EXAMPLE F4

Wettable powder

|  | a) | b) | c) |
|---|---|---|---|
| Active compound | 25% | 50% | 75% |
| Sodium lignosulphonate | 5% | 5% | — |
| Sodium lauryl sulphate | 3% | — | 5% |
| Sodium diisobutylnaphthalene sulphonate | — | 6% | 10% |
| Octylphenol polyethylene glycol ether (7-8 mol of EO) | — | 2% | — |
| Finely divided silicic acid | 5% | 10% | 10% |
| Kaolin | 62% | 27% | — |

Active compound and additives are mixed and the mixture is ground in a suitable mill. This gives wettable powders which can be diluted with water to give suspensions of the desired concentration.

EXAMPLE F5

Emulsion concentrate

| Active compound | 10% |
|---|---|
| Octylphenol polyethylene glycol ether (4–5 mol of EO) | 3% |
| Calcium dodecylbenzenesulphonate | 3% |
| Castor oil polyethylene glycol ether (36 mol of EO) | 4% |
| Cyclohexanone | 30% |
| Xylene mixture | 50% |

Mixing of finely ground active compound and additives gives an emulsion concentrate which, by dilution with water, affords emulsions of the desired concentration.

EXAMPLE F6

Extruder granules

| Active compound | 10% |
|---|---|
| Sodium lignosulphonate | 2% |
| Carboxymethylcellulose | 1% |
| Kaolin | 87% |

Active compound and additives are mixed, the mixture is ground, moistened with water, extruded and granulated, and the granules are dried in a stream of air.

EXAMPLE 7

Coated granules

| Active compound | 3% |
|---|---|
| Polyethylene glycol (MW 200) | 3% |
| Kaolin | 94% |

In a mixer, the finely ground active compound is applied uniformly to the kaolin which has been moistened with polyethylene glycol. This gives dust-free coated granules.

EXAMPLE F8

Suspension concentrate

| Active compound | 40% |
|---|---|
| Ethylene glycol | 10% |
| Nonylphenol polyethylene glycol ether (15 mol of EO) | 6% |
| Sodium lignosulphonate | 10% |
| Carboxymethylcellulose | 1% |
| Aqueous formaldehyde solution (37%) | 0.2% |

EXAMPLE F8-continued

Suspension concentrate

| | |
|---|---|
| Aqueous silicone oil emulsion (75%) | 0.8% |
| Water | 32% |

Mixing of finely ground active compound and additives gives a suspension concentrate which, by dilution with water, affords suspensions of the desired concentration.

BIOLOGICAL EXAMPLES

Example B1

Activity Against *Spodoptera littoralis*

Young soya bean plants are sprayed with an aqueous emulsion spray liquor which comprises 12.5 ppm of active compound, and, after the spray coating has dried on, populated with 10 caterpillars of the first stage of *Spodoptera littoralis* and introduced into a plastic container. 3 days later, the reduction in the population in percent and the reduction in the feeding damage in percent (% activity) are determined by comparing the number of dead caterpillars and the feeding damage between the treated and the untreated plants.

In this test, the compounds of the Tables A1 to A4 and Tables 1 to 48 show good activity. Thus, in particular the compounds A1.1 to A4.2 are more than 80% effective.

Example B2

Activity Against *Spodoptera littoralis*, Systemic

Maize seedlings are placed into the test solution which comprises 12.5 ppm of active compound. After 6 days, the leaves are cut off, placed onto moist filter paper in a Petri dish and populated with 12 to 15 *Spodoptera littoralis* larvae of the $L_1$ stage. 4 days later, the reduction of the population in percent (% activity) is determined by comparing the number of dead caterpillars between the treated and the untreated plants.

In this test, the compounds of the Tables A1 to A4 and Tables 1 to 48 show good activity. Thus, in particular the compounds A1.1 to A4.2 are more than 80% effective.

Example B3

Activity Against *Heliothis virescens*

30-35 eggs of *Heliothis virescens* which are 0- to 24-hour-old are placed onto filter paper in a Petri dish on a layer of synthetic feed. 0.8 ml of the test solution which comprises 12.5 ppm of active compound is then pipetted onto the filter papers. Evaluation is carried out after 6 days. The reduction in the population in percent (% activity) is determined by comparing the number of dead eggs and larvae on the treated and the untreated filter papers.

In this test, the compounds of the Tables A1 to A4 and Tables 1 to 48 show good activity. Thus, in particular the compounds A1.1 to A4.2 are more than 80% effective.

Example B4

Activity Against *Plutella xylostella* Caterpillars

Young cabbage plants are sprayed with an aqueous emulsion spray liquor which comprises 12.5 ppm of the active compound. After the spray coating has dried on, the cabbage plants are populated with 10 caterpillars of the first stage of *Plutella xylostella* and introduced into a plastic container. Evaluation is carried out after 3 days. The reduction in the population in percent and the reduction in the feeding damage in percent (% activity) are determined by comparing the number of dead caterpillars and the feeding damage on the treated and the untreated plants.

In this test, the compounds of the Tables A1 to A4 and Tables 1 to 48 show good activity. Thus, in particular the compounds A1.1 to A4.2 are more than 80% effective.

Example B5

Activity Against *Frankliniella occidentalis*

In Petri dishes, discs of the leaves of beans are placed onto agar and sprayed with test solution which comprises 12.5 ppm of active compound in a spraying chamber. The leaves are then populated with a mixed population of *Frankliniella occidentalis*. Evaluation is carried out after 10 days. The reduction in percent (% activity) is determined by comparing the population on the treated leaves with that of the untreated leaves.

In this test, the compounds of the Tables A1 to A4 and Tables 1 to 48 show good activity. Thus, in particular the compounds A1.1 to A4.2 are more than 80% effective.

Example B6

Activity Against *Diabrotica balteata*

Maize seedlings are sprayed with an aqueous emulsion spray liquor which comprises 12.5 ppm of active compound and, after the spray coating has dried on, populated with 10 larvae of the second stage of *Diabrotica balteata* and then introduced into a plastic container. After 6 days, the reduction in the population in percent (% activity) is determined by comparing the dead larvae between the treated and the untreated plants.

In this test, the compounds of the Tables A1 to A4 and Tables 1 to 48 show good activity. Thus, in particular the compounds A1.1 to A4.2 are more than 80% effective.

Example B7

Activity Against *Tetranychus urticae*

Young bean plants are populated with a mixed population of *Tetranychus urticae* and, after 1 day, sprayed with an aqueous emulsion spray liquor which comprises 12.5 ppm of active compound, incubated at 25° C. for 6 days and then evaluated. The reduction in the population in percent (% activity) is determined by comparing the number of dead eggs, larvae and adults on the treated and on the untreated plants.

In this test, the compounds of the Tables A1 to A4 and Tables 1 to 48 show good activity. Thus, in particular the compounds A1.1 to A4.2 are more than 80% effective.

What is claimed is:

1. A compound of the formula (I)

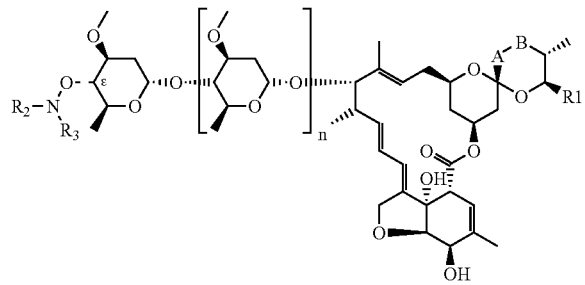

wherein

A-B is —CH=CH— or —CH$_2$—CH$_2$—;

n is 0 or 1;

R$_1$ is C$_1$-C$_{12}$alkyl, C$_3$-C$_8$cycloalkyl or C$_2$-C$_{12}$alkenyl;

R$_2$ and R$_3$ are either, (i) independently from each other, -Q, —C(=Y)-Q, —C(=Y)—O-Q, —C(=Y)—N(R$_6$)-Q, —SO$_2$Q, —SO$_2$N(R$_6$)Q or CN; or (ii) together with the nitrogen atom to which they are bound form a three- to ten-membered ring, which may be monocyclic or bicyclic, which may be saturated or unsaturated, and that may contain, in addition to the aforesaid nitrogen atom, one to two hetero atoms selected from the group consisting of N, O and S, and which is either unsubstituted or independently of one another mono- to pentasubstituted with substituents selected from OH, =O, SH, =S, halogen, CN, SCN, N$_3$, NO$_2$, aryl, C$_1$-C$_{12}$alkyl, C$_3$-C$_8$cycloalkyl, C$_1$-C$_{12}$alkoxy, C$_3$-C$_8$cycloalkoxy, C$_1$-C$_{12}$haloalkoxy, C$_1$-C$_{12}$alkylthio, C$_1$-C$_{12}$cycloalkylthio, C$_1$-C$_{12}$haloalkylthio, C$_1$-C$_6$alkoxy-C$_1$-C$_6$alkyl, C$_2$-C$_8$alkenyl, C$_2$-C$_6$alkenyloxy, C$_2$-C$_6$haloalkenyloxy, C$_2$-C$_8$alkynyl, C$_3$-C$_6$haloalkynyloxy, C$_2$-C$_6$alkenylthio, C$_2$-C$_6$haloalkenylthio, C$_1$-C$_6$alkylsulfinyl, C$_3$-C$_8$cycloalkylsulfinyl, C$_1$-C$_6$haloalkylsulfinyl, C$_3$-C$_8$halocycloalkylsulfinyl, C$_2$-C$_6$alkenylsulfinyl, C$_2$-C$_6$haloalkenylsulfinyl, C$_1$-C$_6$alkylsulfonyl, C$_3$-C$_8$cycloalkylsulfonyl, C$_1$-C$_6$haloalkylsulfonyl, C$_3$-C$_8$halocycloalkylsulfonyl C$_2$-C$_6$alkenylsulfonyl, C$_2$-C$_6$haloalkenylsulfonyl, phenoxy, phenyl-C$_1$-C$_6$alkyl, trialkylsilyl; —C(=O)R$_7$, —O—C(=O)—R$_8$, —NH—C(=O)—R$_8$ and —N(R$_9$)$_2$, wherein the two R$_9$ are independent of each other; or (iii) together are =C(R$_4$)R$_5$;

R$_4$ and R$_5$ are, independently from each other, -Q, —C(=Y)-Q, —C(=Y)—O-Q, —C(=Y)—N(R$_6$)-Q, —SO$_2$Q, —SO$_2$N(R$_6$)Q or CN; or R$_4$ and R$_5$ are together with the carbon atom to which they are bound, a three- to ten-membered alkylene or a four- to seven-membered alkenylene bridge, wherein one CH$_2$ group in the alkylene or alkenylene may have been replaced by O, S or NR$_9$, and which is unsubstituted or mono to tri-substituted;

Y is O or S;

R$_6$ is H, C$_1$-C$_8$alkyl, C$_3$-C$_8$cycloalkyl, C$_2$-C$_8$alkenyl, C$_2$-C$_8$alkynyl, phenyl, benzyl or —C(=O)R$_7$;

Q is H, unsubstituted or mono- to pentasubstituted C$_1$-C$_{12}$alkyl, unsubstituted or mono- to pentasubstituted C$_2$-C$_{12}$alkenyl, unsubstituted or mono- to penta- substituted C$_2$-C$_{12}$alkynyl, unsubstituted or mono- to pentasubstituted C$_3$-C$_{12}$-cycloalkyl, unsubstituted or mono- to pentasubstituted C$_5$-C$_{12}$-cycloalkenyl, unsubstituted or mono- to pentasubstituted aryl, or unsubstituted or mono- to pentasubstituted heterocyclyl;

and wherein the substituents of the alkyl, alkenyl, alkynyl, alkylene, alkenylene, cycloalkyl, cycloalkenyl, aryl and heterocyclyl radicals mentioned under Q, R$_2$, R$_3$, R$_4$, R$_5$ and R$_6$ are selected from the group consisting of OH, =O, SH, =S, halogen, CN, SCN, SF$_5$, N$_3$, NO$_2$, aryl, C$_3$-C$_8$cycloalkyl, C$_1$-C$_{12}$haloalkyl, C$_3$-C$_8$halocycloalkyl, C$_1$-C$_{12}$alkoxy, C$_3$-C$_8$cycloalkoxy, C$_1$-C$_{12}$haloalkoxy, C$_1$-C$_{12}$alkylthio, C$_1$-C$_{12}$cycloalkylthio, C$_1$-C$_{12}$haloalkylthio, C$_1$-C$_6$alkoxy-C$_1$-C$_6$alkyl, C$_1$-C$_6$-alkoxy-C$_1$-C$_6$-alkoxy, C$_2$-C$_8$alkenyl, C$_2$-C$_6$alkenyloxy, C$_2$-C$_6$haloalkenyl, C$_2$-C$_6$haloalkenyloxy, C$_2$-C$_6$alkynyl, C$_2$-C$_6$haloalkynyl, C$_3$-C$_6$alkynyloxy, C$_3$-C$_6$haloalkynyloxy, C$_2$-C$_6$alkenylthio, C$_2$-C$_6$haloalkenylthio, C$_1$-C$_6$alkylsulfinyl, C$_3$-C$_8$cycloalkylsulfinyl, C$_1$-C$_6$haloalkylsulfinyl, C$_3$-C$_8$halocycloalkylsulfinyl, C$_2$-C$_6$alkenylsulfinyl, C$_2$-C$_6$haloalkenylsulfinyl, C$_1$-C$_6$alkylsulfonyl, C$_3$-C$_8$cycloalkylsulfonyl, C$_1$-C$_6$haloalkylsulfonyl, C$_3$-C$_8$halocycloalkylsulfonyl C$_2$-C$_6$alkenylsulfonyl, C$_2$-C$_6$haloalkenylsulfonyl, phenoxy, phenyl-C$_1$-C$_6$alkyl, trialkylsilyl; —C(=O)R$_7$, —O—C(=O)—R$_8$, —NH—C(=O)—R$_8$, —N(R$_9$)$_2$, wherein the two R$_9$ are independent of each other, aryl, benzyl, heterocyclyl, aryloxy, benzyloxy, heterocyclyloxy, arylthio, benzylthio and heterocyclylthio; wherein the aryl, heterocyclyl, aryloxy, benzyloxy, heterocyclyloxy, arylthio, benzylthio and heterocyclylthio radicals are unsubstituted or, depending on the possibilities of substitution on the ring, are mono- to pentasubstituted by substituents selected from the group consisting of OH, =O, SH, =S, halogen, CN, NO$_2$, C$_1$-C$_{12}$alkyl, C$_1$-C$_{12}$hydroxyalkyl, C$_3$-C$_8$cycloalkyl, C$_1$-C$_{12}$haloalkyl, C$_1$-C$_{12}$alkoxy, C$_1$-C$_{12}$haloalkoxy, C$_1$-C$_{12}$alkylthio, C$_1$-C$_{12}$haloalkylthio, C$_1$-C$_6$alkoxy-C$_1$-C$_6$alkyl, dimethylamino-C$_1$-C$_6$alkoxy, C$_2$-C$_8$alkenyl, C$_2$-C$_8$alkynyl, phenoxy, phenyl-C$_1$-C$_6$alkyl; methylenedioxy, —C(=O)R$_7$, —O—C(=O)—R$_8$, —NH—C(=O)R$_7$, —N(R$_9$)$_2$, wherein the two R$_9$ are independent of each other; C$_1$-C$_6$alkylsulfinyl, C$_3$-C$_8$cycloalkylsulfinyl, C$_1$-C$_6$haloalkylsulfinyl, C$_3$-C$_8$halocycloalkylsulfinyl, C$_1$-C$_6$alkylsulfonyl, C$_3$-C$_8$cycloalkylsulfonyl, C$_1$-C$_6$haloalkylsulfonyl and C$_3$-C$_8$halocycloalkylsulfonyl;

R$_7$ is H, OH, SH, —N(R$_9$)$_2$, wherein the two R$_9$ are independent of each other, C$_1$-C$_{24}$alkyl, C$_2$-C$_{12}$alkenyl, C$_1$-C$_8$hydroxyalkyl, C$_1$-C$_{12}$haloalkyl, C$_1$-C$_{12}$alkoxy, C$_1$-C$_{12}$haloalkoxy, C$_1$-C$_6$alkoxy-C$_1$-C$_6$alkyl, C$_1$-C$_6$alkoxy-C$_1$-C$_6$alkoxy, C$_1$-C$_6$alkoxy-C$_1$-C$_6$alkoxy-C$_1$-C$_6$alkyl, C$_1$-C$_{12}$alkylthio, C$_2$-C$_8$alkenyloxy, C$_3$-C$_8$alkynyloxy; aryl, benzyl, heterocyclyl, aryloxy, benzyloxy, heterocyclyloxy; or aryl, benzyl, heterocyclyl, aryloxy, benzyloxy or heterocyclyloxy, which are mono- to tri-substituted in the ring independently of one another by halogen, nitro, C$_1$-C$_6$alkyl, C$_1$-C$_6$alkoxy, C$_1$-C$_6$haloalkyl or C$_1$-C$_6$haloalkoxy;

R$_8$ is H; C$_1$-C$_6$alkyl, which is optionally substituted with one to five substituents selected from the group consisting of halogen, C$_1$-C$_6$alkoxy, hydroxy and cyano; C$_1$-C$_8$-cycloalkyl, aryl, benzyl, heteroaryl; or aryl, benzyl or heteroaryl, which, depending on the possibilities of substitution on the ring, are mono- to trisubstituted by substituents selected from the group consisting of OH, halogen, CN, $NO_2$, $C_1$-$C_{12}$alkyl, $C_1$-$C_{12}$haloalkyl, $C_1$-$C_{12}$alkoxy, $C_1$-$C_{12}$haloalkoxy, $C_1$-$C_{12}$alkylthio and $C_1$-$C_{12}$haloalkylthio; and $R_9$ is H; $C_1$-$C_6$alkyl, which is optionally substituted with one to five substituents selected from the group consisting of halogen, $C_1$-$C_6$alkoxy, hydroxy and cyano; $C_1$-$C_8$-cycloalkyl, aryl, benzyl, heteroaryl; or aryl, benzyl or heteroaryl, which, depending on the possibilities of substitution on the ring, are mono- to trisubstituted by substituents selected from the group consisting of OH, halogen, CN, $NO_2$, $C_1$-$C_{12}$alkyl, $C_1$-$C_{12}$haloalkyl, $C_1$-$C_{12}$alkoxy, $C_1$-$C_{12}$haloalkoxy, $C_1$-$C_{12}$alkylthio and $C_1$-$C_{12}$haloalkylthio;

or, if appropriate, an E/Z isomer, E/Z isomer mixture and/or tautomer thereof, in each case in free form or in salt form.

2. A pesticide composition which contains at least one compound of the formula (I) as described in claim 1 as active compound and at least one auxiliary.

3. A method for controlling pests comprising applying a composition as described in claim 2 to the pests or their habitat.

4. A process for preparing a composition as described in claim 2 comprising intimately mixing and/or grinding the active compound with at least one auxiliary.

5. A method for protecting plant propagation material, wherein the propagation material or the location where the propagation material is planted is treated, comprising applying a composition as described in claim 2.

6. A plant propagation material treated in accordance with the method described in claim 5.

* * * * *